(12) United States Patent
Roth et al.

(10) Patent No.: US 10,842,743 B2
(45) Date of Patent: Nov. 24, 2020

(54) MODIFIED HYALURONIC ACID HYDROGELS AND PROTEINS FOR THE TIME-CONTROLLED RELEASE OF BIOLOGIC AGENTS

(71) Applicant: THE REGENTS OF THE UNIVERSITY OF CALIFORNIA, Oakland, CA (US)

(72) Inventors: Michael D. Roth, Los Angeles, CA (US); Airi Harui, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/091,604

(22) PCT Filed: Apr. 7, 2017

(86) PCT No.: PCT/IB2017/052035
§ 371 (c)(1),
(2) Date: Oct. 5, 2018

(87) PCT Pub. No.: WO2017/175200
PCT Pub. Date: Oct. 12, 2017

(65) Prior Publication Data
US 2019/0240154 A1    Aug. 8, 2019

Related U.S. Application Data

(60) Provisional application No. 62/422,130, filed on Nov. 15, 2016, provisional application No. 62/320,136, filed on Apr. 8, 2016.

(51) Int. Cl.
*A61K 9/06*    (2006.01)
*A61K 47/36*   (2006.01)
(Continued)

(52) U.S. Cl.
CPC .............. *A61K 9/06* (2013.01); *A61K 9/0019* (2013.01); *A61K 38/47* (2013.01); *A61K 45/06* (2013.01);
(Continued)

(58) Field of Classification Search
CPC .... C07K 16/2818; A61K 47/36; A61K 47/14; A61K 9/06; A61K 38/47; A61K 9/0019;
(Continued)

(56) References Cited

U.S. PATENT DOCUMENTS 3,970,429 A   7/1976 Updike
4,211,664 A   7/1980 Dixon et al.
(Continued)

FOREIGN PATENT DOCUMENTS

AU           748850    10/1999
WO    WO 2006/056464   6/2006
(Continued)

OTHER PUBLICATIONS

G.D. Prestwich. Hyaluronic Acid-Based Clinical Biomaterials Derived for Cell and Molecule Delivery in Regenerative Medicine. J. Control Release (2011), 155(2), 18 page reprint. (Year: 2011).*
(Continued)

*Primary Examiner* — Sean C. Barron
(74) *Attorney, Agent, or Firm* — Norton Rose Fulbright US LLP

(57) ABSTRACT

Hyaluronic acid-based hydrogels, solutions for preparing such, and methods pertaining thereunto are disclosed with properties that include self-resorption, extended release of biologically active agents, and/or decreased degradation, denaturation, and/or functional inactivation of biologically active agents.

20 Claims, 15 Drawing Sheets

(51) Int. Cl.

| | | |
|---|---|---|
| *C07K 16/28* | (2006.01) | |
| *A61L 27/54* | (2006.01) | |
| *A61L 27/52* | (2006.01) | |
| *A61L 27/20* | (2006.01) | |
| *A61P 35/00* | (2006.01) | |
| *A61K 9/00* | (2006.01) | |
| *A61K 45/06* | (2006.01) | |
| *A61K 38/47* | (2006.01) | |
| *A61K 47/14* | (2017.01) | |
| *A61K 47/42* | (2017.01) | |
| *A61K 39/00* | (2006.01) | |

(52) U.S. Cl.
CPC .............. *A61K 47/14* (2013.01); *A61K 47/36* (2013.01); *A61K 47/42* (2013.01); *A61L 27/20* (2013.01); *A61L 27/52* (2013.01); *A61L 27/54* (2013.01); *A61P 35/00* (2018.01); *C07K 16/2818* (2013.01); *A61K 2039/505* (2013.01); *A61K 2039/54* (2013.01); *A61K 2039/545* (2013.01); *A61L 2300/256* (2013.01); *A61L 2300/426* (2013.01); *A61L 2400/06* (2013.01); *C07K 16/2803* (2013.01); *C07K 16/2878* (2013.01); *C07K 16/2896* (2013.01)

(58) Field of Classification Search
CPC .. A61K 47/42; A61K 45/06; A61K 2039/545; A61K 2039/505; A61K 2039/54; A61L 27/54; A61L 27/20; A61L 27/52; A61L 2300/426; A61L 2400/06; A61L 2300/256; A61P 35/00; C08L 67/04
See application file for complete search history.

(56) References Cited

U.S. PATENT DOCUMENTS

| | | | |
|---|---|---|---|
| 4,912,032 | A | 3/1990 | Hoffman et al. |
| 5,552,304 | A | 9/1996 | Lee et al. |
| 5,700,915 | A | 12/1997 | Abrams et al. |
| 5,716,612 | A | 2/1998 | Rybak et al. |
| 6,391,937 | B1 | 5/2002 | Beuhler et al. |
| 6,838,081 | B1 | 1/2005 | Roth et al. |
| 8,784,893 | B2 | 7/2014 | Daniloff et al. |
| 8,859,523 | B2 | 10/2014 | Prestwich et al. |
| 2003/0148291 | A1 | 8/2003 | Robotti |
| 2005/0106660 | A1 | 5/2005 | Vogt et al. |
| 2005/0245870 | A1 | 11/2005 | Brown |
| 2006/0058510 | A1 | 3/2006 | Skerra et al. |
| 2006/0088908 | A1 | 4/2006 | Skerra et al. |
| 2006/0153919 | A1 | 7/2006 | Metters et al. |
| 2009/0105193 | A1 | 4/2009 | Prestwich et al. |
| 2010/0285564 | A1 | 11/2010 | Skerra et al. |
| 2013/0052155 | A1 | 3/2013 | Marcolongo et al. |
| 2013/0064861 | A1 | 3/2013 | Schartz et al. |
| 2013/0156858 | A1 | 6/2013 | Wikstrom et al. |
| 2014/0315805 | A1 | 10/2014 | Carmichael et al. |
| 2014/0341842 | A1* | 11/2014 | Zarembinski .......... A61K 47/36 424/85.1 |
| 2015/0166962 | A1 | 6/2015 | Gerecht et al. |
| 2015/0210769 | A1* | 7/2015 | Freeman ................ C07K 16/30 424/136.1 |
| 2015/0352156 | A1 | 12/2015 | Jha et al. |

FOREIGN PATENT DOCUMENTS

| | | |
|---|---|---|
| WO | WO 2011/012715 | 2/2011 |
| WO | WO 2014/144885 | 9/2014 |
| WO | WO 2015/044455 | 4/2015 |
| WO | WO 2016/054555 | 4/2016 |

OTHER PUBLICATIONS

Drug Bank ID DB0072—Trastuzumab (Internet Archive Apr. 6, 2015). (Year: 2015).*

Stagg and Allard. Immunotherapeutic approaches in triple negative breast cancer: latest research and clinical prospects.Ther Adv Med Oncol (2013), 5(3), 169-181. (Year: 2013).*

Buhrman et al. Proteolytically activated anti-bacterial hydrogel microspheres. Journal of Controlled Release (2013), 171, 288-295. (Year: 2013).*

Funakoshi et al. Infection risk in breast cancer patients treated with trastuzumab: a systematic review and meta-analysis. Breast Cancer Res Treat (epub. Nov. 2014, 149, 321-330. (Year: 2014).*

Demaria et al. Immune-Mediated Inhibition of Metastases after Treatment with Local Radiation and CTLA-4 Blockade in a Mouse Model of Breast Cancer. Clinical Cancer Research (2005), 11, 728-734. (Year: 2005).*

Censi et al., "Hydrogels for protein delivery in tissue engineering" *Journal of Controlled Release* 2012, 161(2) 680-692.

Extended European Search Report issued in corresponding application No. 17778778.5, dated Oct. 24, 2019.

Xu et al., "Hyaluronidase-incorporated hyaluronic acid-tyramine hydrogels for the sustained release of trastuz" *Journal of Controlled Release* 2015, 216, 47-55.

Biolegend Technical data sheet LEGEND MAX™ Huam GM-CSF ELISA Kit with Precoated Plates, Sep. 11, 2013. URL: < http://www.biolegend.com/legend-max-human-gm-csf-elisa-kit-5828.html >.

Borghaei et al., "Nivolumab versus docetaxel in advanced nonsquamous non-small-cell lung cancer," *N. Engl. J. Med.*, 2015, 373(17):1627-1639.

Cai et al., "Injectable glycosaminoglycan hydrogels for controlled release of human basic fibroblast growth factor," *Biomaterials*, 2005, 26(30):6054-6067.

Certificate of Analysis for Thiol-Modified Gelatin (type B), Vornia Biomaterials, Aug. 16, 2016, 3 pages.

Cumber et al., "Comparative stabilities in vitro and in vivo of a recombinant mouse antibody FcCys fragment and bisFcCys conjugate" *J. Immunology*, 1992, 149B:120-126.

Gettinger et al., "Overall survival and long-term safety of nivolumab (anti-programmed death-1 antibody, BMS-936558, ONO-4538) in patients with previously treated advanced non-small-cell lung cancer," *J. Clin. Oncol.*, 2015, 33:2004-2012.

Hellman et al., "Nivolumab plus ipilimumab as first-line treatment for advanced non-small-cell lung cancer (CheckMate 012): results of an open-label, phase 1 multicohort study," *Lancet Oncol.*, 2017, 18(1):31-41.

Hodi et al., "Combined nivolumab and ipilimumab versus ipilimumab alone in patients with advanced melanoma: 2-year overall survival outcomes in a multicenter, randomized, controlled, phase 2 trial" *Lancet Oncol.*, 2016, 17(11):1558-1568.

Hodi et al., "Improved survival with ipilimumab in patients with metastatic melanoma," *N. Engl. J. Med.*, 2010, 363:711-723.

International Search Report and Written Opinion issued in International Patent Application No. PCT/US201/052035, dated Sep. 8, 2017.

Kohl et al., "Designed to be stable: Crystal structure of a consensus Ankyrin repeat protein" *Proc. Natl. Acad. Sci., U.S.A.*, 2003, 100(4):1700-1705.

Larkin et al., "Combined nivolumab with ipilimumab or monotherapy in untreated melanoma," *N. Engl. J. Med*, 2015, 373(1):23-34.

Ledford, H., "Cocktails for cancer with a measure of immunotherapy," *Nature*, 2016, 532(7598):162-164.

Linch et al., "Combination OX40 agonism/CTLA-4 blockade with HER2 vaccination reverses T-cell anergy and promotes survival in tumor-bearing mice," *Proc. Natl. Acad. Sci. U.S.A.*, 2016, 113(3):E319-327.

McDermott et al., "Survival, durable response, and long-term safety in patients with previously treated advanced renal cell carcinoma receiving nivolumab," *J. Clin. Oncol.*, 2015, 33:2013-2020.

Murali et al., "Antibody like peptidomimetics as large scale immunodetection probes" *Cell Mol. Biol.*, 2003, 49(2):209-216.

Pack et al., "Miniantibodies: use of amphipathic helixes to produce functional, flexibly linked dimeric FC fragments with high avidity in *Escherichia coli*," *Biochem*, 1992, 31:1579-1584.

Page et al., "Immune modulation in cancer with antibodies," *Annu. Rev. Med.*, 2014, 65:185-202.

(56) References Cited

OTHER PUBLICATIONS

Peattie et al.. "Effect of gelatin on heparin regulation of cytokine release from hyaluronan-based hydrogels," *Drug Deliv.*, 2008, 15(6):389-397.
Pike et al., "Heparin-regulated release of growth factors in vitro and angiogenic response in vivo to implanted hyaluronan hydrogels containing VEGF and bFGF" *Biomaterials*, 2006, 27(30):5242-5251.
PolySciTech Technical Blog, Vornia Bran Thiolated Hyaluronic acid now available from PolySciTech, Mar. 4, 2016, URL < http://jgakinainc.blogspot.com/2016/03/vornia-brand-thiolated-hyaluronic-acid.html .>.
Postow et al., "Nivolumab and ipilimumab versus ipilimumab in untreated melanoma," *N. Engl. J. Med.*, 2015, 372(21):2006-2017.
Rakhmilevich et al., "Effective Combination of Innate and Adaptive Immunotherapeutic Approaches in a Mouse Melanoma Model," *J. Immunol.*, 2007, 198(4):1575-1584.
Ribas et al., "Pembrolisumab versus investigator-choice chemotherapy for ipilimumab-refractor melanoma (KEYNOTE-002): a randomized, controlled, phase 2 trial," *Lancet Oncol.*, 2015, 16:908-918.
Schadendorf et al., "Pooled analysis of long-term survival data from phase II and phase III trials of ipilimumab in unresectable or metastatic melanoma," *J. Clin. Oncol.*, 2015, 33(17):1889-1894.
Selby et al., "Preclinical Development of Ipilimumab and Nivolumab Combination Immunotherapy: Mouse Tumor Models, In Vitro functional Studies, and Cynomolgus Macaque Toxicology," *PLoS One.*, 2016, 11(11):e0167251.
Skerra, "Engineered protein scaffolds for molecular recognition" *J. Mol. Recogn.*, 2000, 13:167-187.
Tivol et al., "Loss of CTLA-4 leads to massive lymphoproliferation and fatal multiorgan tissue destruction, revealing a critical negative regulatory role of CTLA-4," *Immunity*, 1995, 3(5):541-547.
Vornia Biomaterials, Vornia Products, Accessed from the Internet on Oct. 25, 2018, URL < http://www.vornia.com/products-page/ >.
Waterhouse et al., "Lymphoproliferative disorders with early lethality in mice deficient in Ctla-4," *Science*, 1995, 270(5238):985-988.
Weber et al., "Nivolumab versus chemotherapy in patients with advanced melanoma who progressed after anti-CTLA-4 treatment (CheckMate 037): a randomized, controlled, open-label, phase 3 trial," *Lancet Oncol.*, 2015, 16:375-384.
Xu et al., "Hyaluronic Acid-Based Hydrogels: from a Natural Polysaccharide to Complex Networks," *Soft Matter*, 2012, 8(12):3280-3294.

\* cited by examiner

A.

B.

MODIFIED HYALURONIC ACID HYDROGELS AND PROTEINS FOR THE TIME-CONTROLLED RELEASE OF BIOLOGIC AGENTS

CROSS-REFERENCE TO RELATED APPLICATIONS

This application is a national phase application under 35 U.S.C. § 371 of International Application No. PCT/IB2017/052035, filed Apr. 7, 2017, which claims the benefit of priority of U.S. Provisional Patent Application No. 62/320,136 filed Apr. 8, 2016, and U.S. Provisional Patent Application No. 62/422,130 filed Nov. 15, 2016. The entire contents of each of the above-referenced disclosures are specifically incorporated herein by reference without disclaimer

STATEMENT REGARDING FEDERALLY SPONSORED RESEARCH

This invention was made with Government support under A1028697, awarded by the National Institutes of Health. The government has certain rights in the invention.

BACKGROUND OF THE INVENTION

1. Field of the Invention

The present invention relates generally to the field of drug delivery. More particularly, it concerns production and use of hydrogels for the time control release of drugs, including biological agents.

2. Description of Related Art

Systemic biologic therapy using protein-based reagents such as antibodies, cytokines, chemokines and growth factors has become clinically viable and many FDA-approved applications have already reached the market. The majority of these are related to cancer immunotherapy and to the treatment of autoimmune disease. However, these therapies usually require the infusion of a large quantity of the given protein reagent in order to achieve adequate systemic exposure and/or to overcome short biologic half-lives. As a result, the cost required to generate systemic doses of these reagents can be prohibitive and side effects/toxicity are common and can be both debilitating and limiting.

For example, recent advances in immunotherapy targeting checkpoint inhibitors such as PD-1 and CTLA-4 are revolutionizing cancer therapy and out-performing conventional chemotherapy for melanoma, lung cancer, and other tumors (Hodi et al. 2010; Schadendorf et al. 2015; Weber et al. 2015; Larkin et al. 2015; Borghaei et al. 2015; Ribas et al. 2015; Gettinger et al. 2015; McDermott et al. 2015). Monoclonal antibodies (mAb) targeting these checkpoint inhibitors enhance antitumor responses by blocking immunosuppressive pathways that are turned on by cancers as an escape mechanism. However, response rates to single reagents remain limited and combination therapy is being actively investigated (Linch et al. 2016). Combining anti-CTLA-4 with anti-PD-1 has demonstrated superior efficacy against melanoma and early clinical data suggest the same for non-small cell lung cancer (NSCLC) (Larkin et al. 2015; Postow et al. 2015). Unfortunately, systemic administration of mAbs targeting checkpoint inhibitors can include serious toxicity that is also magnified by combination therapy (Postow et al. 2015; Page et al. 2014). Severe, and sometimes fatal, autoimmune reactions associated with the infusion of anti-CTLA-4 mAb occur at rates of 15-41% and can include enterocolitis, endocrinopathy, hepatotoxicity, dermatitis and other autoimmune manifestations. These "side-effects" highlight the important role that these pathways play in regulating self-tolerance and autoimmunity (Tivol et al. 1995; Waterhouse et al. 1995). Mechanisms for promoting a more effective balance between antitumor immunity and autoimmune toxicity are needed.

To reduce the costs, side effects, and toxicity, research is being done to find methods and apparatuses to control release of protein-based reagents.

Standard HA-based hydrogels have several features that make them desirable for use as drug delivery depots. HA-based hydrogels are tissue biocompatible, have the potential to polymerize and transition from a liquid to a solid at the site of injection, and are inherently porous, which provides an opportunity for loading them with other molecules or reagents as a reservoir for local delivery. However, while HA-based hydrogels share these desirable features, currently available compositions are not effectively optimized for the delivery of protein-based biologic reagents in a manner that allows the user to adjust the rate of release to match the needs of the biologic condition being treated.

Another limitation of many HA-based hydrogels is that the polymerization process is either too slow, allowing the hydrogel components to diffuse away from the site of injection before a localized tissue depot can be formed, or the process is too fast, making it difficult to effectively mix, prepare and deliver an injection to the desired tissue site.

Further, once polymerized into their gelled state, HA-based hydrogels can persist for weeks to months as a solid mass, ultimately limiting the capacity for repeated injections at the same site or producing unwanted cosmetic or functional consequences due to mass effects that last beyond the time required for the intended therapy. In addition, if an added reagent is bound to the hydrogel and the hydrogel persists without degradation, the added reagents may be trapped and retained within the hydrogel for an extended period beyond their intended therapeutic window, yet released at some delayed time-point that is not appropriate for the intended use.

In addition, it is well accepted that pore size is one of the features of a hydrogel that can contribute to its capacity for retention and controlled delivery of added reagents; however, protein-based biologic reagents can vary over a broad range of molecular weights and sizes, often well below the ranges associated with retention based on the native size of the pores in standard formulations of HA-based hydrogels. Mismatching between the size of the protein-based biologic reagent and the pore size of the hydrogel, and variability between the molecular weight of various different proteins, can produce a significant obstacle that prevents controlled release of the reagent over time.

Thus, there remains a need for methods and apparatuses to control release of protein-based reagents that has not been met by current HA-based hydrogels.

SUMMARY OF THE INVENTION

Many off the problems associated with HA-based hydrogels are disclosed herein. Notably, the disclosure provides novel functionalized HA-based hydrogels capable of effectively retaining and releasing protein-based biologic reagents in a time-controlled manner. It has been demonstrated herein that the HA-based hydrogels can effectively be used in vivo to provide a sustained release of antibodies, such as immune checkpoint inhibitor antibodies. Using the HA-based hydrogels drastically decreased the amount of antibody needed to provide a robust antitumor response when compared to a larger systemic dose. Accordingly, the unwanted side effects/toxicity caused by administering more antibodies can be reduced or avoided.

In some aspects, disclosed herein are compositions capable of forming a HA-based hydrogel. In some instances, the composition can be a liquid composition. In some instances, the composition can form a HA-based hydrogel upon activation of a cross-linking reaction involving functionalized hyaluronic acid and a cross-linking agent. In some instances, the composition contains functionalized hyaluronic acid, a cross-linking agent capable of cross-linking the functionalized hyaluronic, and optionally contains hyaluronidase, a gelatin and/or functionalized gelatin, and/or a biologically active agent. In some instances, the composition contains hyaluronidase. In some instances, the hyaluronidase can be dispersed in the composition. In some instances, the hyaluronidase can be solubilized in the composition. In some instances, the hyaluronidase can be contained in the composition at a concentration capable of increasing the rate of degradation of the hyaluronic acid-based hydrogel when compared to a hyaluronic acid-based hydrogel without hyaluronidase. In some instances, the hyaluronidase can be contained in the composition at a concentration capable of decreasing the rate of degradation, denaturation, and/or functional inactivation of a biologically active agent contained in the formed hyaluronic acid-based hydrogel when compared to a hyaluronic acid-based hydrogel without hyaluronidase.

In some aspects, the composition may contain an amount of functionalized hyaluronic acid and cross-linking agent, wherein the formed hyaluronic acid-based hydrogel is capable of retaining a biologically active agent with a molecular weight within a specific range. In some aspects, the composition can contain 0.2% w/v to 1.0% w/v of functionalized hyaluronic acid and 0.1% w/v to 2.0% w/v of cross-linking agent, wherein the formed hyaluronic acid-based hydrogel is capable of retaining a biologically active agent with a molecular weight of 10 kD to 300 kD in the hyaluronic acid-based hydrogel. In some instances, the formed hyaluronic acid-based hydrogel is capable of retaining at least a specific amount of the biologically active agent in the hyaluronic acid-based hydrogel for a specific period of time. In some instances, the formed hyaluronic acid-based hydrogel is capable of retaining at least 20% of the biologically active agent in the hyaluronic acid-based hydrogel for 24 hours.

In some aspects, the functionalized hyaluronic acid and/or the cross-linking agent are capable of chemically binding a biologically active agent. In some instances, the biologically active agent is bound to a linker that is capable of chemically binding to the functionalized hyaluronic acid and/or the cross-linking agent. In some instances, the biologically active agent comprises a glutathione-S-transferase (GST) tag and the functionalized hyaluronic acid and/or cross-linking agent contains a sulfahydral group.

In some aspects, the composition contains a compound or composition capable of slowing degradation, denaturation, and/or functional inactivation of a biologically active agent when compared to hyaluronic acid-based hydrogel without the compound or composition capable of slowing the degradation, denaturation, and/or functional inactivation of the biologically active agent. In some aspects, the composition contains gelatin and/or functionalized gelatin. In some aspects, the gelatin and/or functionalized gelatin is contained at a concentration capable of slowing degradation, denaturation, and/or functional inactivation of a biologically active agent when compared to a hyaluronic acid-based hydrogel without gelatin or functionalized gelatin. In some aspects, the composition contains hyaluronidase. In some aspects, the composition contains hyaluronidase at a concentration capable of slowing degradation, denaturation, and/or functional inactivation of a biologically active agent when compared to a hyaluronic acid-based hydrogel without hyaluronidase.

In another aspect, disclosed herein is a hyaluronic acid-based hydrogel formed from any of the compositions described herein. In some instances the hyaluronic acid-based hydrogel contains a porous cross-linked polymeric matrix of functionalized hyaluronic acid that is cross-linked with a cross-linking agent.

In yet another aspect, herein is disclosed a hyaluronic acid-based hydrogel containing a porous cross-linked polymeric matrix of functionalized hyaluronic acid that is cross-linked with a cross-linking agent and includes an average pore size volume that is capable of entrapping and retaining a biologically active agent within the pores of the polymeric matrix; and a biologically active agent entrapped in the pores of the polymeric matrix, wherein the biologically active agent is capable of being released in a controlled manner from the hydrogel when the hydrogel is administered to a subject. In some instances, the hyaluronic acid-based hydrogel contains hyaluronidase evenly dispersed and/or solubilized throughout the porous cross-linked polymeric matrix. In some instances, the hyaluronidase is contained in an amount effective to increase the rate of degradation of the matrix when compared to a HA-based hydrogel without hyaluronidase evenly dispersed and/or solubilized therein. In some instances, the hyaluronic acid-based hydrogel contains 1 unit/ml to 200 units/ml of hyaluronidase.

In some aspects, the cross-linking agent is a functionalized polyethylene glycol. In some instances, the functionalized hyaluronic acid is cross-linked through a thiol group on the functionalized hyaluronic acid and an acrylate group on the functionalized polyethylene glycol.

In another aspect, the hyaluronic acid-based hydrogel or composition disclosed herein contains 0.2% w/v to 1.0% w/v of the functionalized hyaluronic acid and 0.1% w/v to 2.0% w/v of the cross-linking agent.

In yet another aspect, the cross-linking density of the porous cross-linked polymeric matrix is specifically matched to the size and/or molecular weight of the biologically active agent in order to control the rate of release of the biologically active agent from the hydrogel.

In some aspects, the hyaluronic acid-based hydrogel or composition disclosed herein contains a functionalized gelatin that is covalently bound to the functionalized hyaluronic acid, wherein the functionalized gelatin protects against degradation, denaturation, and/or functional inactivation of the biologically active agent when compared to a hyaluronic acid-based hydrogel without functionalized gelatin. In some instances, the hyaluronic acid-based hydrogel or composition contains 0.1% w/v to 0.8% w/v of the functionalized gelatin. In some instances, the activity of a biologically active agent entrapped in the formed hyaluronic acid-based hydrogel does not decrease by more than 40% compared to the activity of the biological agent that has not been incorporated into the hyaluronic acid-based hydrogel.

In some aspects, the hyaluronic acid-based hydrogel or composition disclosed herein contains one or more biologically active agent(s). In some instances, the biologically active agent is chemically bound to the functionalized hyaluronic acid through a linker group. In some instances, the linker group is a glutathione-S-transferase (GST) tag.

In some instances, the biologically active agent(s) have a molecular weight of at least, at most, and/or about 1000 kD, 1000, 900, 800, 700, 600, 500, 400, 300, 200, 190, 180, 170, 160, 150, 140, 130, 120, 110, 100, 90, 80, 70, 60, 50, 40, 30, 20, 10, 9, 8, 7, 6, 5, 4, 3, 2, 1, 0.9, 0.8, 0.7, 0.6, 0.5, 0.4, 0.3, 0.2, 0.1, less than 0.1 kD, and any range derivable therein. In some instances, preferred embodiments have a molecular weight of 10 kD to 300 kD, 100 kD to 200 kD, 80 kD to 200 kD, 130 kD to 170 kD, 140 kD to 160 kD, about 150 kD, or 150 kD, or any range derivable therein.

In some instances, the biologically active agent is a peptide or a protein, or a fusion peptide or protein thereof, or is a viral or bacterial particle. In some instances, the biologically active agent is an antibody or a fusion antibody, a cytokine or a fusion cytokine, a chemokine or a fusion chemokine, a growth factor or a fusion growth factor, or a hormone or fusion hormone. In some instances, the biologically active agent is a human Fc conjugated protein.

In some instances, the biologically active agent is an antibody. The antibody may be, for example, an antibody fragment, single domain, monoclonal, and/or polyclonal antibody. The antibody may be a mouse, rabbit, human, humanized, or chimeric antibody. The antibody may be a purified antibody or recombinant. In other embodiments, there may be chemical modifications to the polypeptide, such as the addition of one or more chemical modifications or moieties.

In some instances, the biologically active agent is a therapeutic antibody targeting an immune check point inhibitor, and/or human Fc conjugated cytokine with immune activating properties. In some instances, the therapeutic antibody targeting an immune check point inhibitor is an anti CTLA-4 antibody, anti PD-1 antibody, and/or anti PD-L1 antibody. It is contemplated that any of these may be specifically excluded in an embodiment. The hyaluronic acid-based hydrogel or composition disclosed herein can contain multiple immune check point inhibitor antibodies, such as, but not limited an anti CTLA-4 antibody and an anti PD-1 antibody.

In some aspects, disclosed herein are methods for administering the hyaluronic acid-based hydrogel or compositions disclosed herein to a subject by topically applying, surgically implanting, and/or injecting the hydrogel to the subject. In some instances, administration is by parentally injecting the hydrogel or composition into to the subject. In some instances, the biologically active agent is released from the hydrogel or composition in a time controlled manner. In some instances, the biologically active agent is released over a period of 1 to 30 days.

In some aspects, disclosed herein is a method for treating a subject by administering to the subject any one of the hyaluronic acid-based hydrogel or composition disclosed herein containing one or more biologically active agent(s). The method can be for treating a cancer in a subject. The cancer can be a tumor. The tumor can be at least one of lung cancer, non-small cell lung cancer (NSCLC), prostate cancer, ovarian cancer, testicular cancer, brain cancer, glioblastoma, pediatric tumors, germ cell tumors, skin cancer, melanoma, colon cancer, rectal cancer, gastric cancer, esophageal cancer, tracheal cancer, head and neck cancer, pancreatic cancer, liver cancer, breast cancer, lymphoid cancer, leukemia, cervical cancer, and vulvar cancer. In some embodiments, the tumor is a solid tumor. In some embodiments, the cancer is metastatic. In some instances, the hyaluronic acid-based hydrogel or composition disclosed herein administered to the subject contains one or more biologically active agent(s) effective against a cancer. In some embodiments, the method further comprises administering a second biologically active agent(s) that is different than the biologically active agent contained in the hydrogel or composition disclosed herein. The second biologically active agent can be encapsulated in a second hyaluronic acid-based hydrogel or composition disclosed herein. In some embodiments, the second biologically active agent is not encapsulated in a hyaluronic acid-based hydrogel or composition disclosed herein. In some embodiments, the method further comprises administering the hyaluronic acid-based hydrogel or composition disclosed herein with a second therapy.

In some embodiments, the one or more biologically active agent(s) and/or one or more second biologically active agent(s) is an antibody. In some embodiments, the biologically active agent(s) and/or one or more second biologically active agent(s) is a checkpoint inhibitor. The checkpoint inhibitor may be one known in the art or described herein. In some embodiments, the checkpoint inhibitor is an antagonist of TGIT, CTLA-4, PD-1, or PD-L1. In some embodiments, the checkpoint inhibitor is a small molecule, an antibody, a peptide, or a nucleic acid. In some embodiments, more than one checkpoint inhibitor is contained in the hyaluronic acid-based hydrogel or composition disclosed herein. It is also contemplated that one or more of the embodiments discussed herein may be specifically excluded. In some embodiments, the method further comprises administering a checkpoint inhibitor that is not contained in a hyaluronic acid-based hydrogel or composition disclosed herein. In some embodiments, the checkpoint inhibitor is selected from Ipilmumab; Nivolumab; Lambrolizumab; anti-PD-L1 antibodies BMS-936559, MSB0010718C, MPDL3280A, and MedI-4736; and anti-PD-1 antibody pembrolizumab/MK-3475, pidilizumab, AMP-224, and RG7446; agonistic anti-4-1bb antibody; agonistic anti-CD27 antibody; agonistic anti-GTIR antibody; agonistic anti-OX40 antibody; and antagonistic anti-TIM3 antibody. It is specifically contemplated that one or more of these checkpoint inhibitors may be excluded in an embodiment.

In some embodiments, the one or more biologically active agent(s) and/or one or more second biologically active agent(s) is a chemotherapeutic agent. The chemotherapeutic agent can be contained in a hyaluronic acid-based hydrogel or composition disclosed herein and/or administered without being contained in a hyaluronic acid-based hydrogel or composition disclosed herein. In some embodiments, the methods exclude the administration of, or the compositions exclude, one or more chemotherapeutic agents described herein.

In some embodiments, a ionizing radiation is administered to the subject. The ionizing radiation (IR) can be administered locally to a cancerous region. In some embodiments, the dose of ionizing radiation is greater than 20 Gy. In some embodiments, the IR is administered in one, two, or three doses. In some embodiments, IR is administered weekly in one dose per week, wherein the dose is greater than 20 Gy. In some embodiments, 2 Gy of ionizing radiation is administered for a total of thirty-five times. In some embodiments, 20 Gy of ionizing radiation is administered for a total of three times. In some embodiments, 34 Gy is administered in one dose. In some embodiments, the dosing regimen is not repeated until at least 1, 2, 3, 4, 5, 6, 7, 8, 9, 10, 11, or 12 months (or any range derivable therein) have passed. In some embodiments, the dosing regimen is one described herein.

In some embodiments, the subject has been previously treated for cancer. In some embodiments, the subject was resistant to the previous cancer treatment. In some embodiments, the subject was determined to be a poor responder to the cancer treatment.

The terms "subject" and "patient" are used interchangeably. In some embodiments, the subject is a mammal. In some embodiments, the subject is a human. In some embodiments, the subject is a mouse, rat, rabbit, dog, donkey, or a laboratory test animal such as fruit fly, zebrafish, etc.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

In some aspects, disclosed herein are methods for protecting a biologically active agent from degradation, denaturation, and/or functional inactivation within a HA-based hydrogel matrix by (a) adding and/or increasing the concentration of gelatin or functionalized gelatin as a component of the HA-based hydrogel matrix, (b) increasing the concentration of cross-linking reagents, (c) adding and/or increasing the concentration of hyaluronidase, or any combination or all of (a) to (c).

In some aspects, disclosed herein are methods for decreasing the rate of release of a biologically active agent from a hyaluronic acid-based hydrogel by (a) increasing the cross-linking density of the porous cross-linked polymeric matrix, (b) increasing the size of the biologically active agent, (c) chemically binding the biologically active agent to the functionalized hyaluronic acid, or any combination or all of (a) to (c). In some instances, the size of the biologically active agent is increased by fusing a peptide or protein fusion partner to the biologically active agent. In some instances, the peptide or protein fusion partner is an antibody or a fragment thereof. In some instances, the biologically active agent contains a linker group that is chemically bound to the functionalized hyaluronic acid and/or cross-linker.

In some aspects, disclosed herein are methods for increasing the rate of release of a biologically active agent from a porous cross-linked polymeric matrix of a HA-based hydrogel by (a) decreasing the cross-linking density of the porous cross-linked polymeric matrix, (b) incorporating hyaluronidase into the porous cross-linked polymeric matrix, or a combination of (a) and (b).

In some aspects, disclosed herein are methods for increasing self-resorption of a porous cross-linked polymeric matrix of a HA-based hydrogel by incorporating hyaluronidase into the porous cross-linked polymeric matrix, wherein the hyaluronidase is evenly dispersed and/or solubilized throughout the porous cross-linked polymeric matrix. In some instances, the concentration of hyaluronidase is adjusted based on the desired rate of the self-resorption.

In some aspects, disclosed herein are methods for making a hyaluronic acid-based hydrogel disclosed herein by obtaining a biologically active agent, a cross-linking agent, hyaluronic acid and/or functionalized hyaluronic acid, optionally hyaluronidase, and optionally gelatin and/or functionalized gelatin, combining the biologically active agent and optionally the hyaluronidase to make Combination I; combining the cross-linking agent with the Combination I to make Combination II; combining the hyaluronic acid and/or functionalized hyaluronic acid and optionally the gelatin and/or functionalized gelatin to make Combination III; combining Combination II and Combination III to produce a final hyaluronic acid-based hydrogel combination; and optionally activating or increasing the rate of a cross-linking reaction between at least the cross-linking agent and the hyaluronic acid and/or functionalized hyaluronic acid. In some instances, the Combinations I, II, III, and the final hyaluronic acid-based hydrogel combination are prepared at room temperature. In some instances, the Combinations I, II, and III are solutions in water, saline, or phosphate buffered saline.

In some aspects, disclosed herein are kits for forming a hyaluronic acid-based hydrogel containing functionalized hyaluronic acid, a cross-linking agent capable of cross-linking the functionalized hyaluronic, hyaluronidase, optionally a gelatin and/or functionalized gelatin, optionally a biologically active agent, and optionally instructions comprising directions to combine at least the hyaluronic acid, cross-linking agent, and hyaluronidase prior to formation of the hyaluronic acid-based hydrogel. In some instances, the kit contains instructions containing directions to combine at least the hyaluronic acid, cross-linking agent, and hyaluronidase prior to formation of the hyaluronic acid-based hydrogel, and directions to combine at least the hyaluronic acid and hyaluronidase in concentrations capable of controlling the rate of degradation of the hyaluronic acid-based hydrogel. In some instances, the kit contains instructions containing directions to combine at least the hyaluronic acid, cross-linking agent, and hyaluronidase prior to formation of the hyaluronic acid-based hydrogel, and directions to combine at least the hyaluronidase and the hyaluronic acid, cross-linking agent, and/or the optional biologically active agent in concentrations capable of slowing the rate of degradation, denaturation, and/or functional inactivation of the biologically active agent when compared to a hyaluronic acid-based hydrogel without hyaluronidase. In some instances, the kit contains instructions containing directions to combine at least the hyaluronic acid, cross-linking agent, and hyaluronidase prior to formation of the hyaluronic acid-based hydrogel, and directions to combine at least the hyaluronidase and the hyaluronic acid, cross-linking agent, and/or the optional biologically active agent in concentrations capable of retaining at least 60% of the activity of a biologically active agent entrapped in the formed hyaluronic acid-based hydrogel compared to the activity of the biological agent that has not been incorporated into the hyaluronic acid-based hydrogel.

In some aspects, disclosed herein are kits for forming a hyaluronic acid-based hydrogel containing functionalized hyaluronic acid, a cross-linking agent capable of cross-linking the functionalized hyaluronic, optionally a hyaluronidase, optionally a gelatin and/or functionalized gelatin, optionally a biologically active agent, and instructions containing directions to combine at least the hyaluronic acid and cross-linking agent in concentrations capable of retaining a molecule and/or a molecule with a molecular weight and/or size in the hyaluronic acid-based hydrogel. In some instances, the instructions contain directions to combine at least the hyaluronic acid and cross-linking agent in concentrations capable of retaining a molecule and/or a molecule with a molecular weight and/or size in the hyaluronic acid-based hydrogel for a period of time. In some instances, the instructions contain directions to combine at least the hyaluronic acid and cross-linking agent in concentrations capable of retaining a molecule and/or a molecule with a molecular weight of 10 kD to 300 kD in the hyaluronic acid-based hydrogel for 1 to 30 days.

In some aspects, disclosed herein are kits for forming a hyaluronic acid-based hydrogel containing functionalized hyaluronic acid, a cross-linking agent capable of cross-linking the functionalized hyaluronic, optionally a hyaluronidase, optionally a gelatin and/or functionalized gelatin, optionally a biologically active agent, and optionally instructions containing directions to combine at least the hyaluronic acid and cross-linking agent to form a hyaluronic acid-based hydrogel, wherein the functionalized hyaluronic acid and/or the cross-linking agent are capable of chemically binding a biologically active agent. In some instances, the biologically active agent contains a glutathione-S-transferase (GST) tag and the functionalized hyaluronic acid and/or cross-linking agent contains a sulfahydral group.

In some aspects, disclosed herein are kits for forming a hyaluronic acid-based hydrogel containing functionalized hyaluronic acid, a cross-linking agent capable of cross-linking the functionalized hyaluronic, a gelatin and/or functionalized gelatin, optionally hyaluronidase, optionally a biologically active agent, and optionally instructions comprising directions to combine at least the hyaluronic acid and cross-linking agent to form the hyaluronic acid-based hydrogel. In some instances, the kit contains instructions containing directions to combine at least the hyaluronic acid and cross-linking agent to form the hyaluronic acid-based hydrogel, and wherein the instructions further contain directions to combine at least the gelatin and/or functionalized gelatin at a concentration capable of slowing the rate of degradation, denaturation, and/or functional inactivation of the biologically active agent when compared to a hyaluronic acid-based hydrogel without gelatin or functionalized gelatin. In some instances, the kit contains instructions containing directions to combine at least the hyaluronic acid and cross-linking agent to form the hyaluronic acid-based hydrogel, and wherein the instructions further contain directions to combine at least the gelatin and/or functionalized gelatin at a concentration capable of retaining at least 60% of the activity of a biologically active agent entrapped in the formed hyaluronic acid-based hydrogel compared to the activity of the biological agent that has not been incorporated into the hyaluronic acid-based hydrogel.

In some aspects, disclosed herein are injectable reagents comprising three to five defined components, the reagent being capable of forming a hyaluronic acid-based hydrogel matrix, wherein the presence and concentration of these defined components are specifically adjusted for and matched with the size and/or binding affinity of an incorporated biologically active agent for the purposes of a) retaining the biologically active agent within the hydrogel matrix, b) protecting the biologically active agent from modification, degradation, denaturation, and/or functional inactivation, and/or c) releasing the biologically active agent in a time-controlled manner in which the duration of release can be adjusted from a period of hours to days to match an intended biologic application. In some instances, one of the three to five defined components is hyaluronidase, wherein hyaluronidase is dispersed in the formed hyaluronic acid-based hydrogel. In some instances, the hyaluronidase is solubilized in the formed hyaluronic acid-based hydrogel. In some instances, the hyaluronidase is at a concentration capable of increasing the rate of degradation of the formed hyaluronic acid-based hydrogel when compared to a hyaluronic acid-based hydrogel without hyaluronidase. In some instances, the hyaluronidase is comprised at a concentration capable of decreasing the rate of degradation, denaturation, and/or functional inactivation of a biologically active agent comprised in the formed hyaluronic acid-based hydrogel when compared to a hyaluronic acid-based hydrogel without hyaluronidase. In some instances, two of the defined components are functionalized hyaluronic acid and a cross-linking agent comprising 0.2% w/v to 1.0% w/v of functionalized hyaluronic acid and 0.1% w/v to 2.0% w/v of cross-linking agent, wherein the formed hyaluronic acid-based hydrogel is capable of retaining a biologically active agent with a molecular weight of 10 kD to 300 kD in the hyaluronic acid-based hydrogel. In some instances, the formed hyaluronic acid-based hydrogel is capable of retaining at least 20% of the biologically active agent in the hyaluronic acid-based hydrogel for 24 hours. In some instances, two of the defined components are functionalized hyaluronic acid and a cross-linking agent, wherein the functionalized hyaluronic acid and/or cross-linking agent are capable of chemically binding a biologically active agent. In some instances, the biologically active agent comprises a glutathione-S-transferase (GST) tag and the functionalized hyaluronic acid and/or cross-linking agent contains a sulfahydral group. In some instances, one of the defined components is gelatin and/or functionalized gelatin. In some instances, the gelatin and/or functionalized gelatin is comprised at a concentration capable of slowing degradation, denaturation, and/or functional inactivation of a biologically active agent when compared to hyaluronic acid-based hydrogel without gelatin or functionalized gelatin. In some instances, the injectable reagent comprises five defined components that are a) a functionalized hyaluronic acid; b) a cross-linking agent capable of cross-linking the functionalized hyaluronic acid; c) a gelatin or functionalized gelatin; d) a hyaluronidase; and e) a biologically active agent or fusion construct thereof.

In some aspects, disclosed herein is hyaluronic acid-based hydrogels formed from any of the injectable reagents disclosed herein. In some instances, the hyaluronic acid-based hydrogels formed contains a porous cross-linked polymeric matrix of functionalized hyaluronic acid that is cross-linked with a cross-linking agent. Publicly and/or commercially available matrices are contemplated in embodiments discussed herein.

"GLYCOSIL®" is a thiol-modified hyaluronic acid and a constituent of native extracellular matrix (ECM). GLYCOSIL® and thiol-modified hyaluronic acid are commercially available. Non-limiting examples of commercial sources for GLYCOSIL® and thiol-modified hyaluronic acid include ES Cell International (ESI-BIO™) and BioTime, Inc. Non-limiting examples of commercial sources for thiol-modified hyaluronic acid also include Fast-Gelling Thiol-Modified Hyaluronic Acid (HA-SH) from Vornia Biomaterials.

"GELIN-S®" is thiol-modified gelatin (denatured collagen). GELIN-S®" and thiol-modified gelatin are commercially available. Non-limiting examples of commercial sources for GELIN-S® and thiol-modified gelatin include ES Cell International (ESI-BIO™) and
BioTime, Inc. Non-limiting examples of commercial sources for thiol-modified gelatin also include Thiolated Gelatin (Gel-SH) from Vornia Biomaterials.

"EXTRALINK®" is thiol-reactive cross-linker (polyethylene glycol diacrylate). EXTRALINK® and polyethylene glycol diacrylate (PEGDA) are commercially available. Non-limiting examples of commercial sources for EXTRALINK® and PEGDA include ES Cell International (ESI-BIO™) and BioTime, Inc. Non-limiting examples of commercial sources for PEGDA also include Sigma and PolySciences Inc.

Hyaluronidase refers to a family of enzymes defined by their capacity to degrade the multimeric form of hyaluronic acid into its component disaccharides and oligosaccharides. Hyaluronidase is commercially available. Non-limiting examples of commercial sources for hyaluronidase include FDA-approved human recombinant hyaluronidase with the trade name HYLENEX® and as a purified protein available from a number of commercial venders.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is also contemplated that one or more of the embodiments discussed herein may be specifically excluded in a particular embodiment; for example, a negative limitation is contemplated in certain embodiments.

The methods and apparatus of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the methods and apparatus of the present invention is the ability releasing protein-based biologic reagents in a time-controlled manner.

The terms "chemically bound," "chemically bind," and "chemically bond," and its variations include ionic bonds, covalent bonds, and/or bonds through Van der Waals forces.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A: GM-CSF release is different when hydrogels are formulated only with GLYCOSIL® (GLYCOSIL® hydrogel) or with the combination of GLYCOSIL® and GELIN-S® (GLYCOSIL®+GELIN-S® hydrogel). GM-CSF (0.5 ug) was incorporated into the two different hydrogels yielding a final hydrogel volume of 0.125 ml according to the following formulations: 1) GLYCOSIL® hydrogel composed of GLYCOSIL® [0.8% w/v] and EXTRALINK® [0.2% w/v]) and 2) GLYCOSIL®+GELIN-S® hydrogel composed of GLYCOSIL® [0.4% w/v], GELIN-S® [0.4% w/v], and EXTRALINK® [0.2% w/v]). Hydrogels were incubated in 1.0 ml of release media at 37° C. for 7 days with exogenous HAse (1000 units) added for the last 24 hours to lyse the hydrogels. The levels of GM-CSF released into media were measured by ELISA. Each condition was prepared in triplicate. Representative experiments: n>5. FIG. 2B: Impact of different Hystem-C constituents on the integrity of cytokine. Recombinant human GM-CSF was incubated with PBS (control) or specific hydrogel components: GLYCOSIL® (0.4% w/v), GLYCOSIL® (0.8% w/v), Gelatin (0.4% w/v), a combination of GLYCOSIL® and Gelatin (0.4% w/v each) or EXTRALINK® (0.2% w/v) in volume 0.125 ml PBS (same as volume of hydrogels) for 30 min at room temperature followed by incubation in release media at 37° C. for 4 hours, and the levels of GM-CSF was determined by ELISA. The experiment was performed in triplicates. Representative experiment: n=3. FIG. 2C: IL4 release by GLYCOSIL® hydrogel (top) and GLYCOSIL®+GELIN-S® hydrogel (bottom). Recombinant human IL4 (20 ug) was formulated into GLYCOSIL® hydrogel (GLYCOSIL® [0.8% w/v], EXTRALINK® [0.2% w/v]) and 1 ml of release media was added/replaced at each time point. Recombinant human IL4 (5 ug) was formulated into GLYCOSIL®+GELIN-S® hydrogel (GLYCOSIL® [0.4% w/v], GELIN-S® [0.4% w/v], EXTRALINK® [0.2% w/v]) and 1 ml of release media was added/replaced at each time point. Hydrogels were incubated in release media at 37° C. for 7 days with HAse (1000 units) added for the last 24 hours to lyse the hydrogels. The levels of IL4 released into media were measured by ELISA. (Note: these are from slightly different conditions. The amount of IL-4 added to the gel in GM-CSF release by GLYCOSIL® hydrogel was 20 ug, while that added in GLYCOSIL®+GELIN-S® hydrogel used 5 ug, with the cumulative release expressed as a percent of control for each assay. FIG. 2D: Higher concentrations of EXTRALINK® promote more effective recovery of added protein. GST tagged human IL-4 (GST-IL-4, 0.5 ug) or fusion protein of human Fc region and GM-CSF (Fc-GM-CSF, 0.5 ug) was formulated into hydrogel with different concentration of EXTRALINK® (GLYCOSIL® [0.4% w/v], GELIN-S® [0.4% w/v], EXTRALINK® [0.2, 0.8% or 1.2% w/v]). Hydrogels were incubated in release media at 37° C. for 3 days, additional HAse (1000 units) added to culture for the last 24 hours, and cytokines levels released into media were measured by ELISA.

Figure 3A:
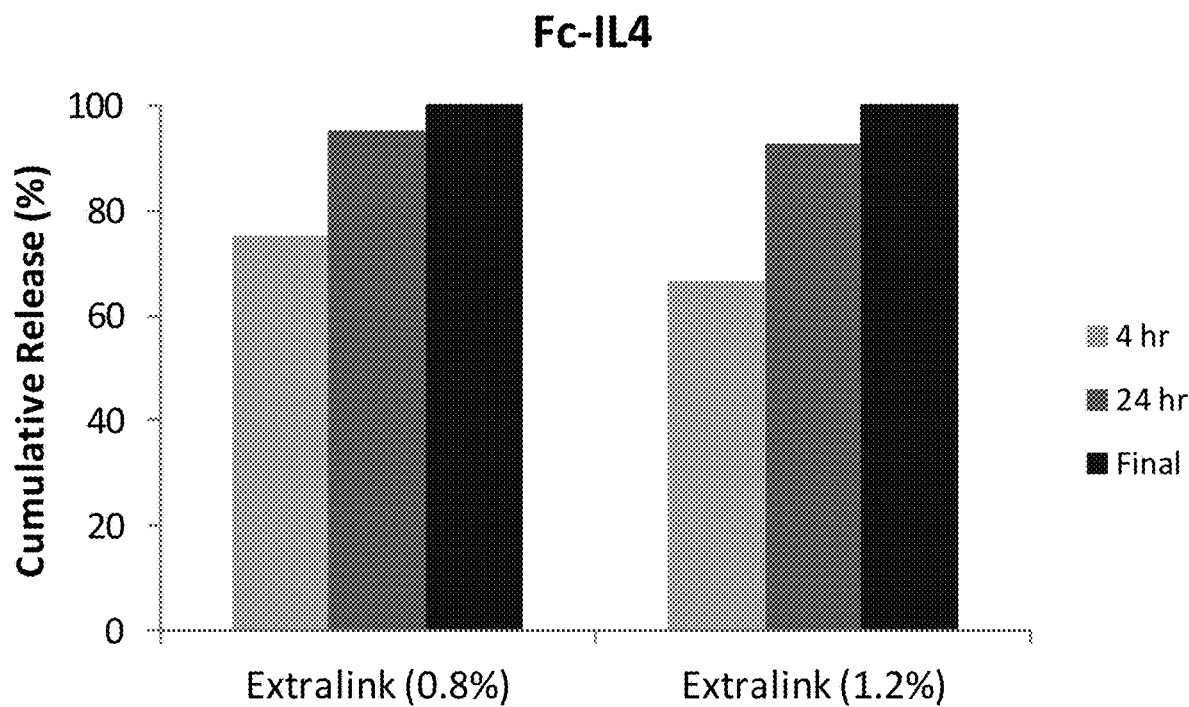
Figure 3B:
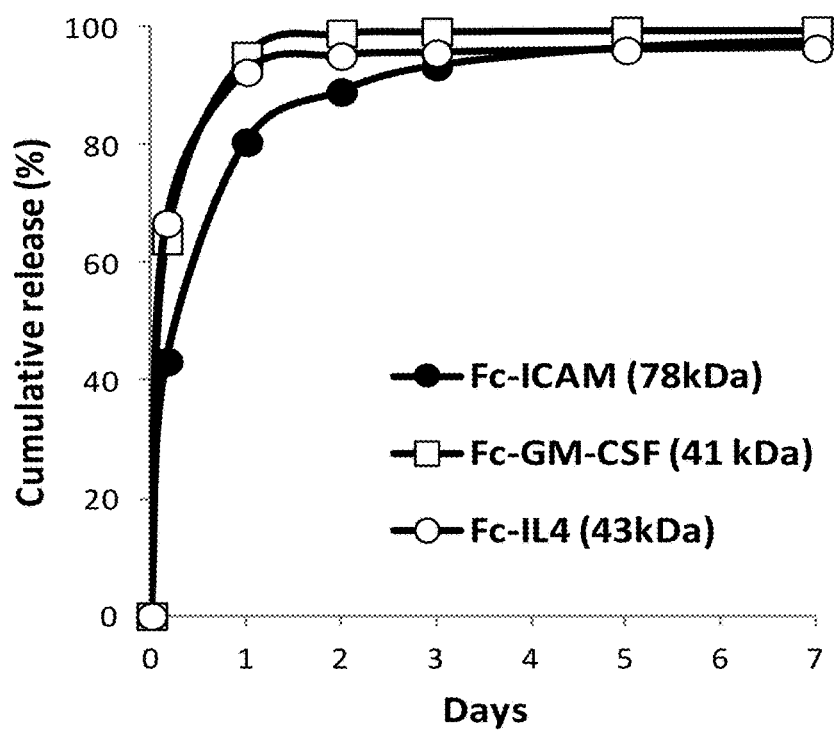
Figure 3C:
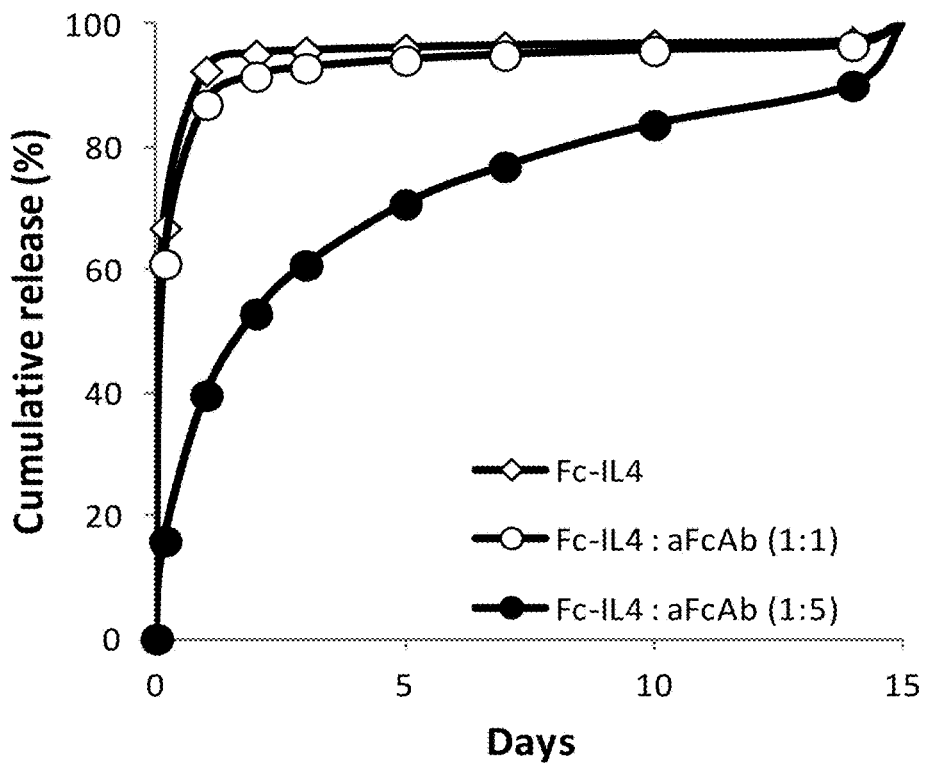
Figure 3D:
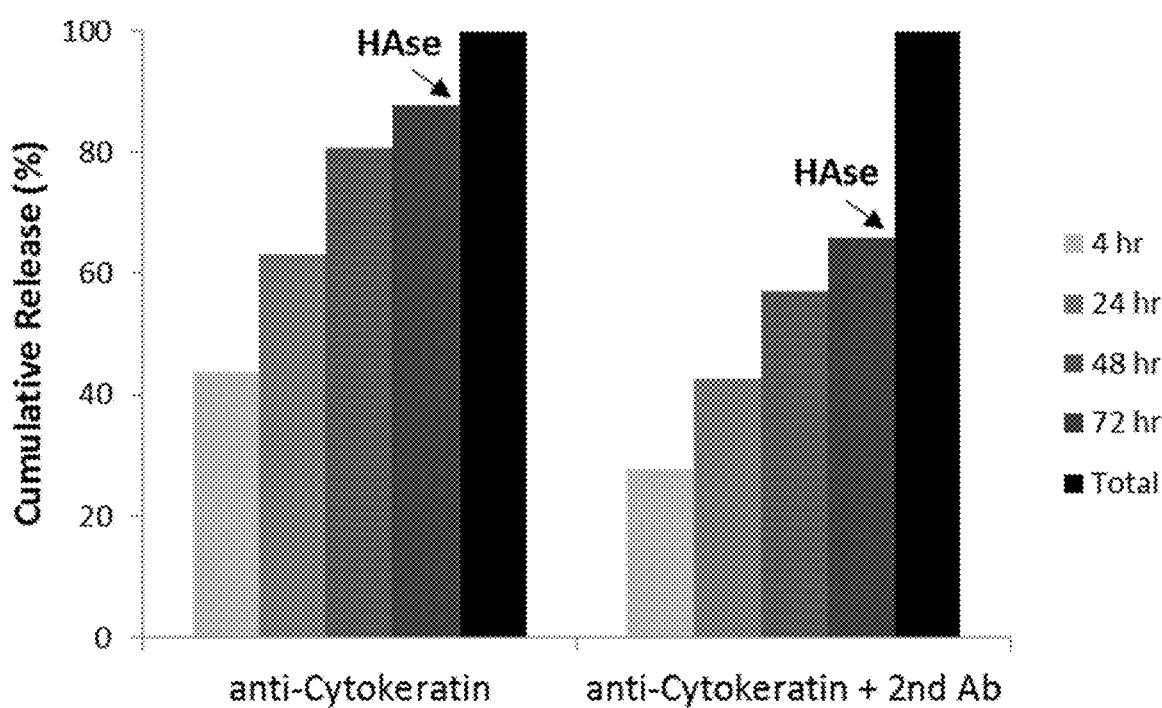

FIGS. 3A-3D: FIG. 3A: Concentration of EXTRALINK® affects cytokine release kinetics. Fusion protein of human antibody Fc region and human IL4 (Fc-IL-4, 0.5 ug) was encapsulated into GLYCOSIL®+GELIN-S® hydrogels containing low and high concentration of EXTRALINK® (GLYCOSIL® [0.4% w/v], GELIN-S® [0.4% w/v], EXTRALINK® [0.8% w/v] or [1.2% w/v]) and 1 ml of release media was added/replaced at each time point. Hydrogels were incubated in release media at 37° C. for 3 days with HAse (1000 units) added for the last 24 hours to lyse the hydrogels. The levels of IL4 released into media were measured by ELISA. Total Release of IL4 from each gel represents 100%. (FIGS. 3B and 3C) Molecular weight/size affects cytokine release kinetics. FIG. 3B: Fusion proteins of human antibody Fc region and human cytokines, Fc-GM-CSF (41 kDa), Fc-IL4 (43 kDa) or Fc-ICAM (78 kDa), were encapsulated into GLYCOSIL®+GELIN-S® hydrogel (GLYCOSIL® [0.4% w/v], GELIN-S® [0.4% w/v], EXTRALINK® [1.2% w/v]) respectively and 1 ml of release media was added/replaced at each time point. FIG. 3C: Fc-IL4 alone, Fc-IL4 pre-incubated with anti-Fc antibody in 1:1 or 1:5 ratio were encapsulated into GLYCOSIL®+GELIN-S® hydrogel (GLYCOSIL® [0.4% w/v], GELIN-S® [0.4% w/v], EXTRALINK® [1.2% w/v]) respectively and 1 ml of release media was added/replaced at each time point. Hydrogels were incubated in release media at 37° C. for 7 (FIG. 3A) or 15 (FIG. 3B) days with HAse (1000 units) added for the last 24 hours to lyse the hydrogels. The levels of cytokines released into media were measured by ELISA. Total Release of each cytokine represents 100%. FIG. 3D: Antibody release by HA-based hydrogel. FITC-conjugated anti-Cytokeratin antibodies (Mouse IgG, 0.5 ug) alone or pre-incubated with anti-mouse IgG antibody at 1:5 ratio were encapsulated into GLYCOSIL®+GELIN-S® hydrogel (GLYCOSIL® [0.4% w/v], GELIN-S® [0.4% w/v], EXTRALINK® [1.2% w/v]) respectively and 1 ml of release media were added/replaced at each time point. Hydrogels were incubated in release media at 37° C. for 4 days with HAse (1000 units) added for the last 24 hours to lyse the hydrogels. The levels of FITC-Cytokeratin released into media were measured by fluorescent plate reader. Total Release of antibody represents 100%.

Figure 4A:
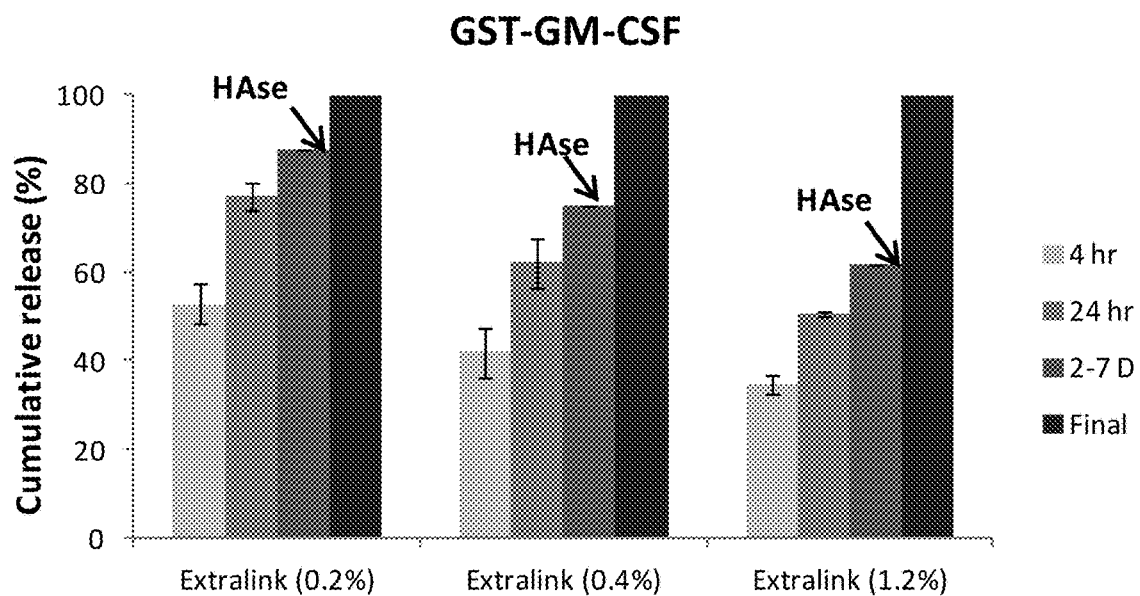
Figure 4B:
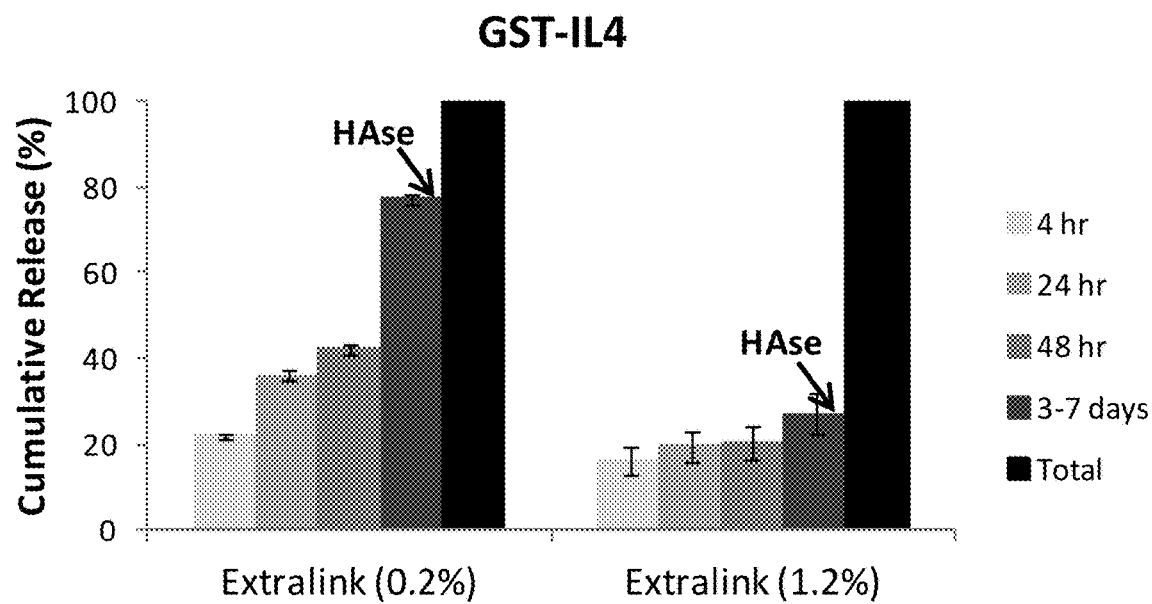

FIGS. 4A-4B: Concentration of EXTRALINK® affects GST-tagged cytokine release kinetics and retention. GST-tagged human cytokines, (FIG. 4A) GST-GM-CSF (0.5 ug) or (FIG. 4B) GST-IL4 (0.5 ug) were encapsulated into GLYCOSIL®+GELIN-S® hydrogel with low to high concentration of EXTRALINK® (GLYCOSIL® [0.4% w/v], GELIN-S® [0.4% w/v], EXTRALINK® [0.2%-1.2% w/v]) respectively and 1 ml of release media was added/replaced at various time points. Hydrogels were incubated in release media at 37° C. for 8 days with HAse (1000 units) added for the last 24 hours to lyse the hydrogels. The levels of cytokines released into media were measured by ELISA. Total Release of each cytokine represents 100%.

Figure 5A:
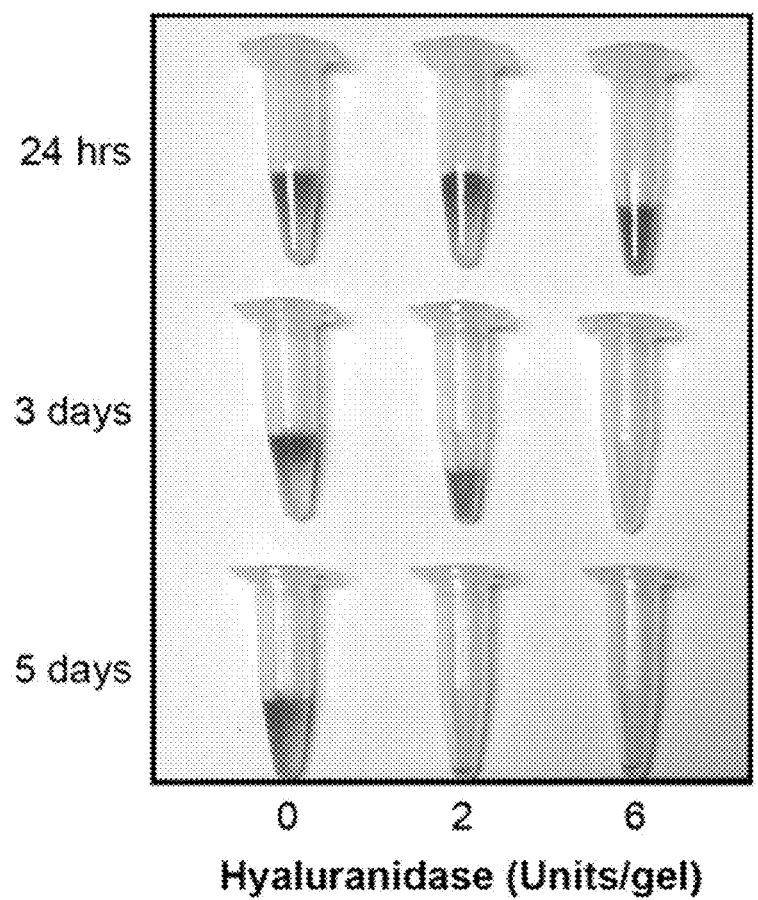
Figure 5B:
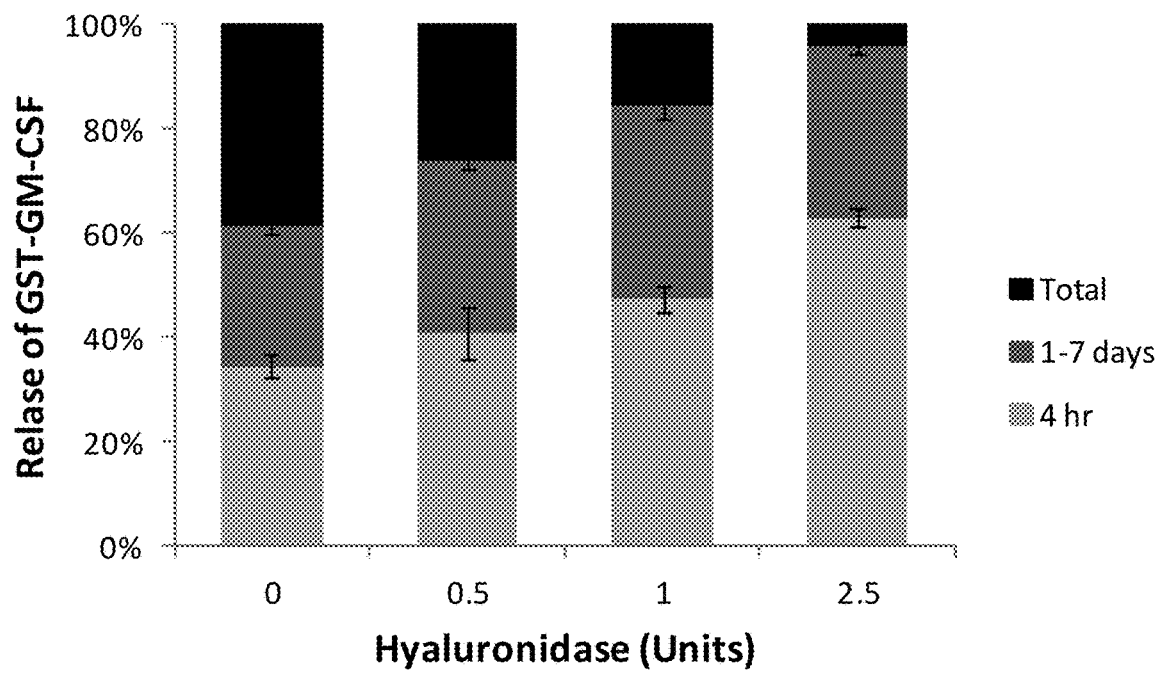
Figure 5C:
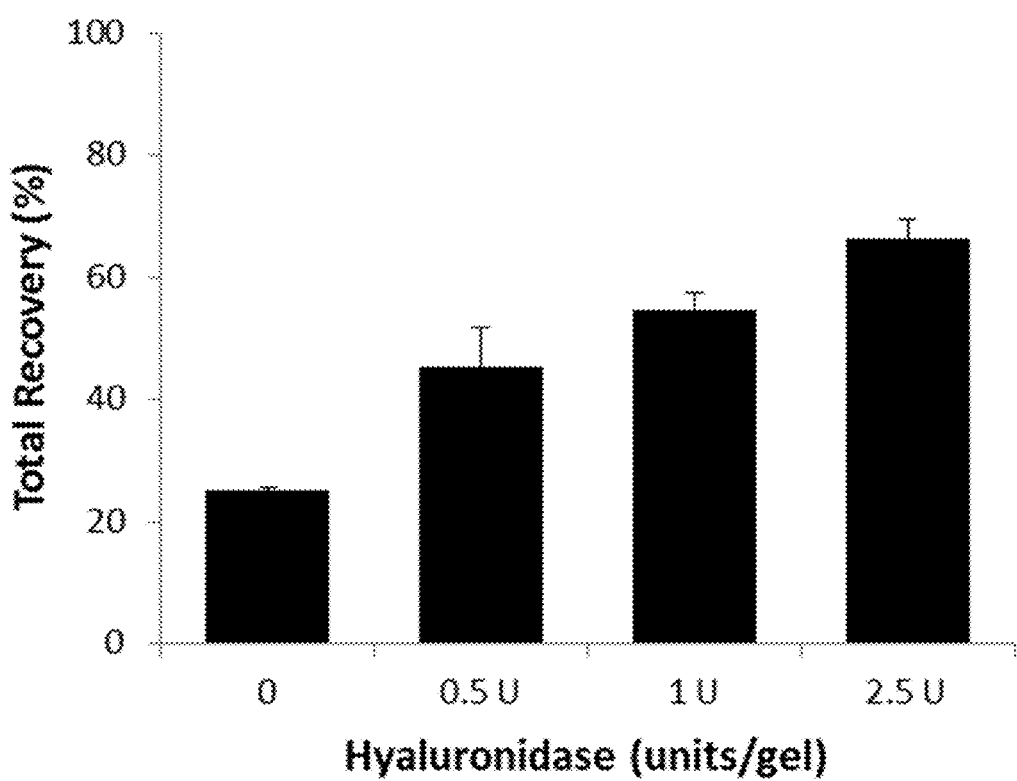

FIGS. 5A-5C: FIG. 5A: Controlled hydrogel resorption using hyaluronidase incorporated as a hydrogel constituent. Hydrogels (GLYCOSIL® 0.4% w/v, EXTRALINK® 0.2% w/v) formulated with different amounts of HAse (0, 2, 6 units) were cultured with release media at 37° C. At designated times after the initiation of gelation (24 hrs, 3 d, 5 d) the media was removed and a drop of trypan blue dye was added to visualize the volume of remaining gel. FIG. 5B: Controlled release of GST-GM-CSF by incorporating HAse into hydrogel. GST-GM-CSF (0.5 ug) were encapsulated into hydrogel (GLYCOSIL® [0.4% w/v], GELIN-S® [0.4% w/v], EXTRALINK® [1.2% w/v]) with 0-2.5 units of HAse and 1 ml of release media was added/replaced at various time points. Hydrogels were incubated in release media at 37° C. for 8 days with HAse (1000 units) added for the last 24 hours to lyse the hydrogels. The levels of cytokines released into media were measured by ELISA. Total Release of each cytokine represents 100%. FIG. 5C: Higher concentrations of HAse promote more effective recovery of added protein. GST-GM-CSF was formulated into hydrogel (GLYCOSIL® [0.4% w/v], GELIN-S® [0.4% w/v], EXTRALINK® [1.2% w/v]) with HAse (0, 0.5, 1, or 2.5 units/gel). Hydrogels were incubated in release media at 37° C. for 7 days, additional HAse (1000 units) added to culture for the last 24 hours, and cytokines levels released into media were measured by ELISA. Data is presented based on the total release of GST-GM-CSF from hydrogels without HAse as 100%.

Figure 6A:
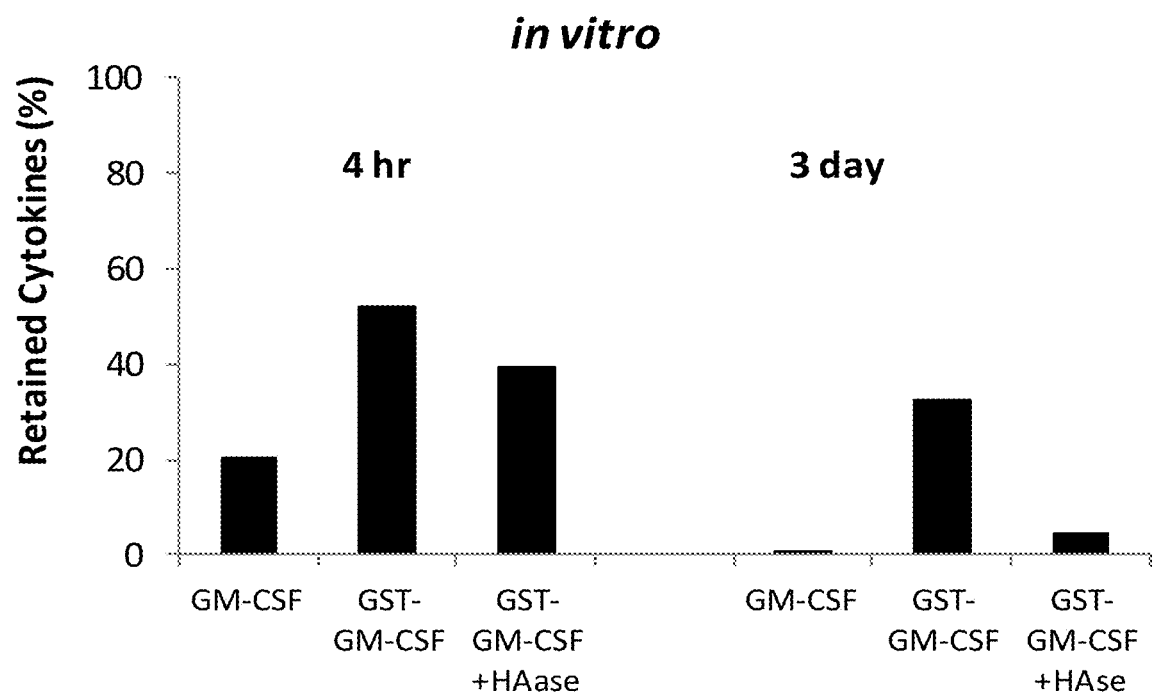
Figure 6B:
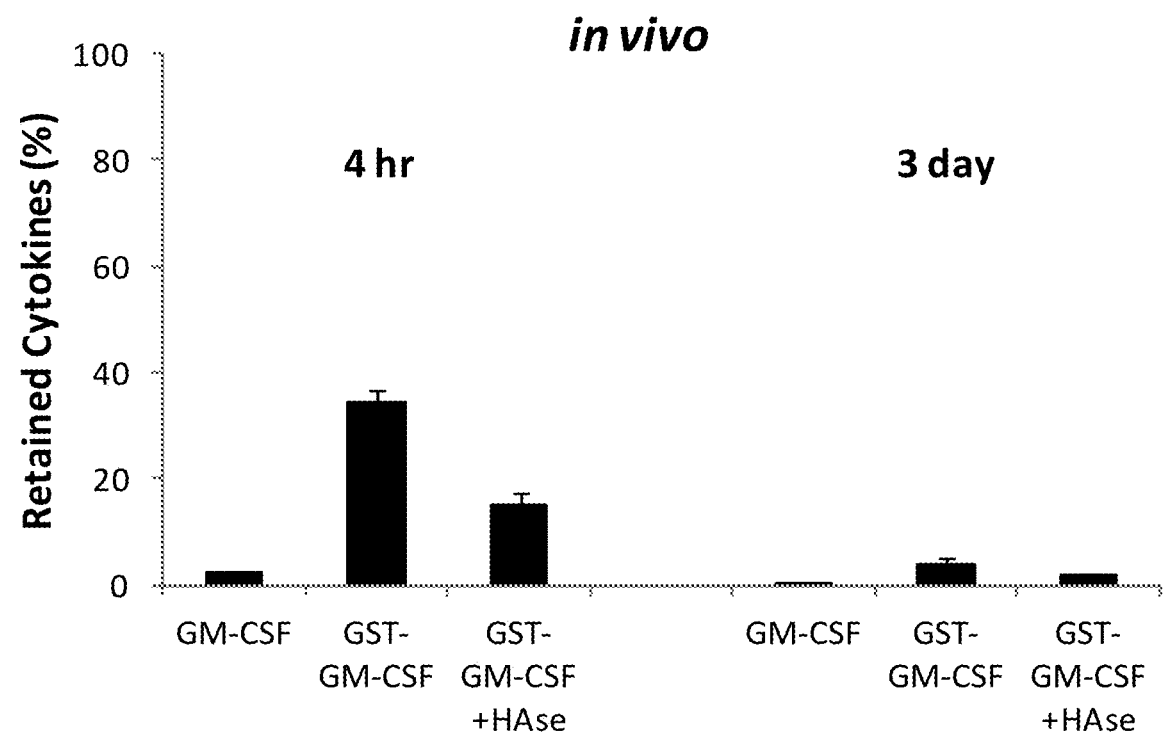

FIGS. 6A-6B: Cytokine release kinetics in vitro (FIG. 6A) and in vivo (FIG. 6B). GM-CSF, GST-GM-CSF or GM-CSF with HAse (2.5 units) was formulated into hydrogel (GLYCOSIL® [0.4% w/v], GELIN-S® [0.4% w/v], EXTRALINK® [1.2% w/v]). FIG. 6A: For in vitro assay, hydrogels were incubated in 1 ml release media at 37° C. for 4 hours or 3 days, media were exchanged with media contain HAse (1000 units) followed by 24 hours incubation until hydrogel lysis. FIG. 6B: For in vivo assay, hydrogels were mixed and injected into mice by s.c. injection within 5 minutes, excised out 4 hours or 3 days later and incubated with media contain HAse (1000 units) for 24 hours until lysis. Levels of cytokines were determined by ELISA. Experiment was performed in triplicates. Representative experiment: n=3.

Figure 7:
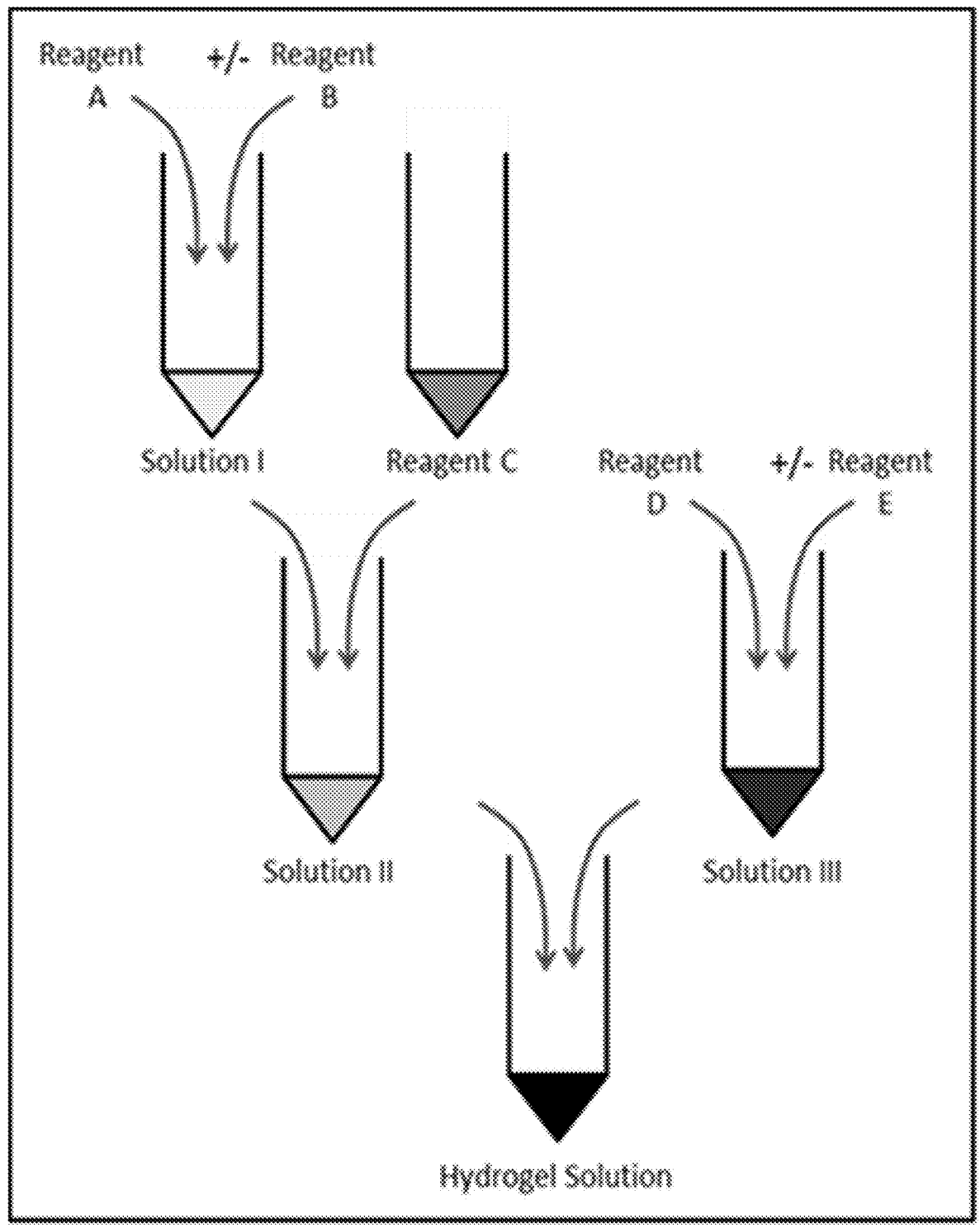

FIG. 7: Non-limiting example of steps for preparing Hyaluronic Acid (HA)-based hydrogels loaded with desired biologically active agent.

Figure 8:
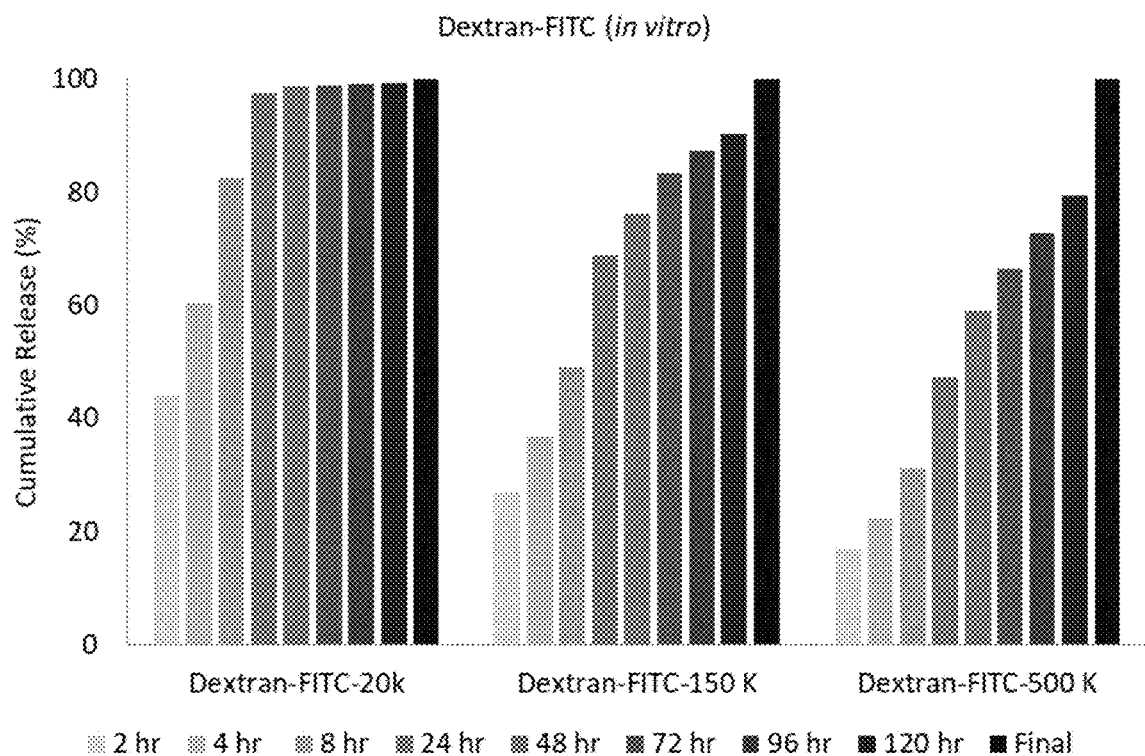
Figure 8:
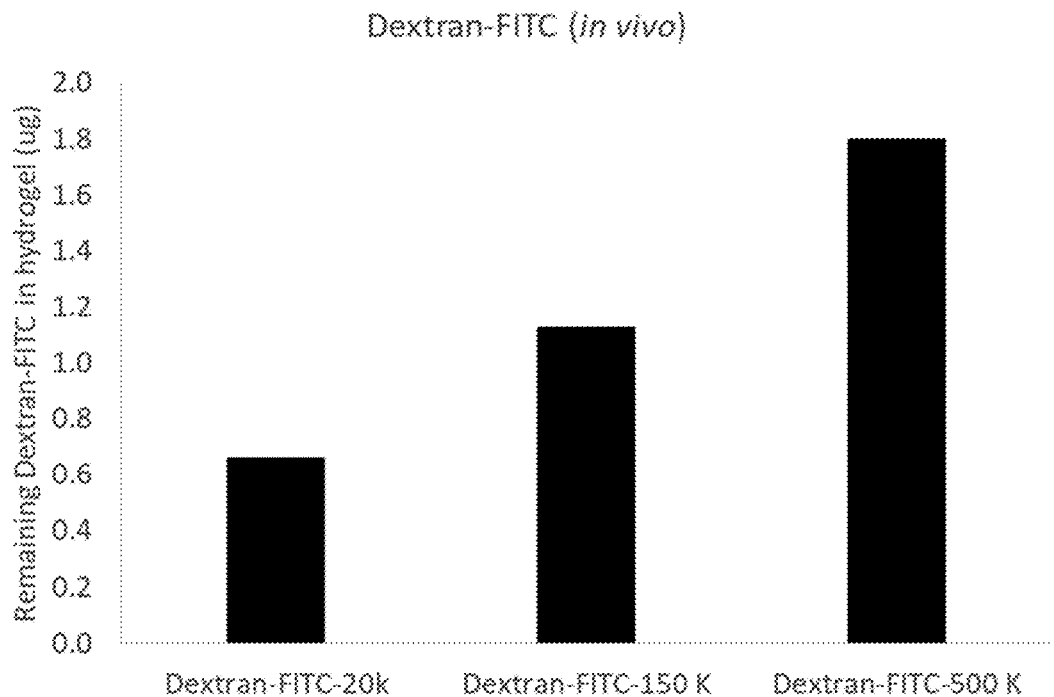

FIG. 8: The molecular weight of an incorporated payload is inversely related to the rate of release from the hydrogel in vitro (A) and in vivo (B). Three commercially available FITC-labeled dextran constructs (5 μg each) with defined molecular weights of 20 kDa, 150 kDa, and 500 kDa were loaded into a GLYCOSIL® hydrogel (GLYCOSIL® [0.8% w/v], EXTRALINK® [1.2% w/v]). For in vitro experiment (A), hydrogels prepared from an initial 150 ul volume were incubated in 1 ml release media at 37° C. The release media was collected, the volume measured, and the same volume of fresh media replaced at various time points as indicated. Exogenous HAse was added at the 120 hr time point to lyse the hydrogel and release any remaining molecules from the hydrogel. The amount of FITC-labeled Dextran recovered within each aliquot of release media was determined by fluorescent plate reader using dilutions prepared from each construct (20 kDa, 150 kDa, 500 kDa) to produce a standard curve. For in vivo experiments (B), the same hydrogel formulations were injected into the subcutaneous tissue over the flanks of C57B1/6 mice and recovered 4 hrs later by surgical excision. Exogenous tissue was dissected away and hydrogels placed into release media.

Figure 9:
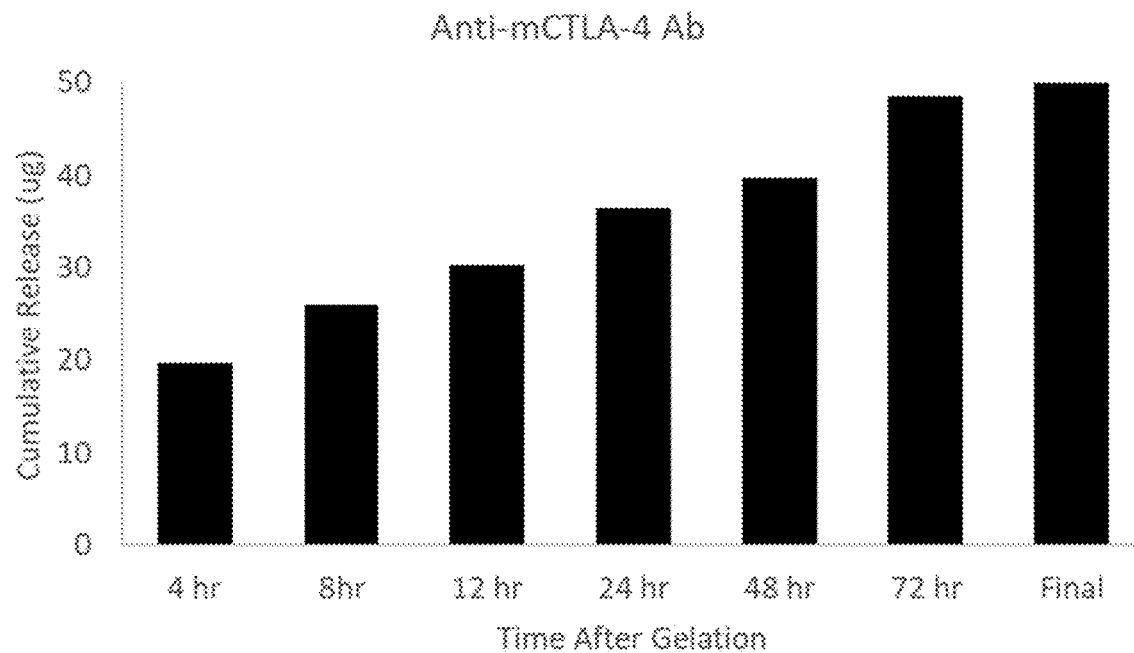
Figure 9:
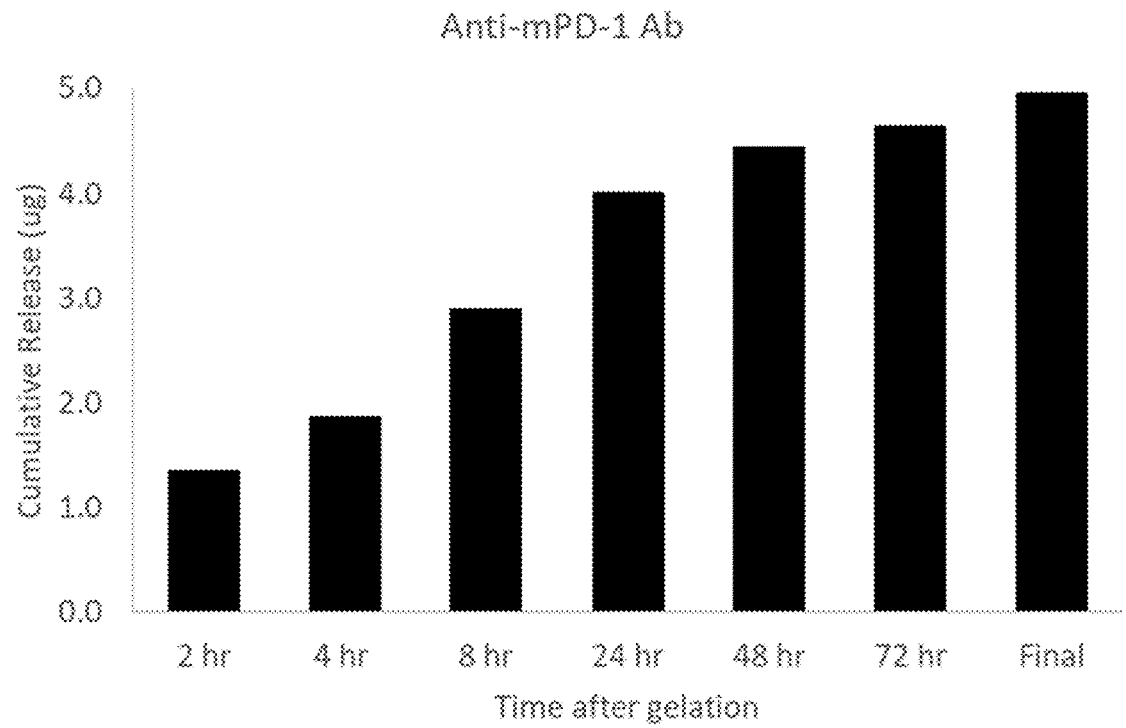

FIG. 9: Incorporation of functional immune checkpoint inhibitor antibodies into a GLYCOSIL® Hydrogel results in the controlled and near-complete release of antibody over several days with retention of target binding affinity. Monoclonal anti-mouse antibodies specific for murine CTLA-4 (unlabeled, 50 ug/hydrogel) (A) or for murine PD-1 (FITC-labeled, 5 ug/hydrogel) (B) were incorporated into a GLYCOSIL® hydrogel (GLYCOSIL® [0.8% w/v], EXTRALINK® [1.2% w/v]). Hydrogels were incubated in 10 ml (for anti-mCTLA-4 Ab) or 1 ml (for anti-mPD-1/FITC Ab) of release media at 37° C. The release media was collected, the volume measured, and the same volume of fresh media replaced at various time points as indicated. Exogenous HAse was added at the 72 hr time point to lyse the hydrogel and release any remaining molecules from the hydrogel. The levels of anti-mCTLA-4 Ab were measure by ELISA, based on affinity binding to plate-bound murine CTLA-4, and the levels of anti-mPD-1 Ab were measured by fluorescent plate reader.

Figure 10A:
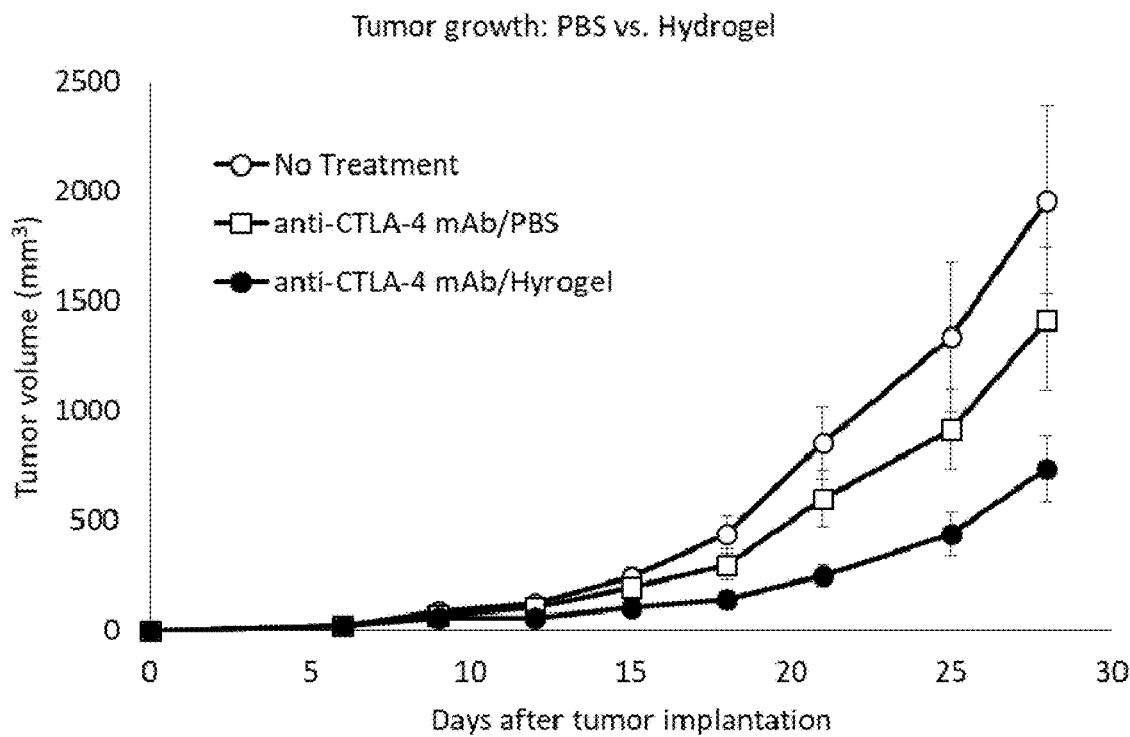
Figure 10B:
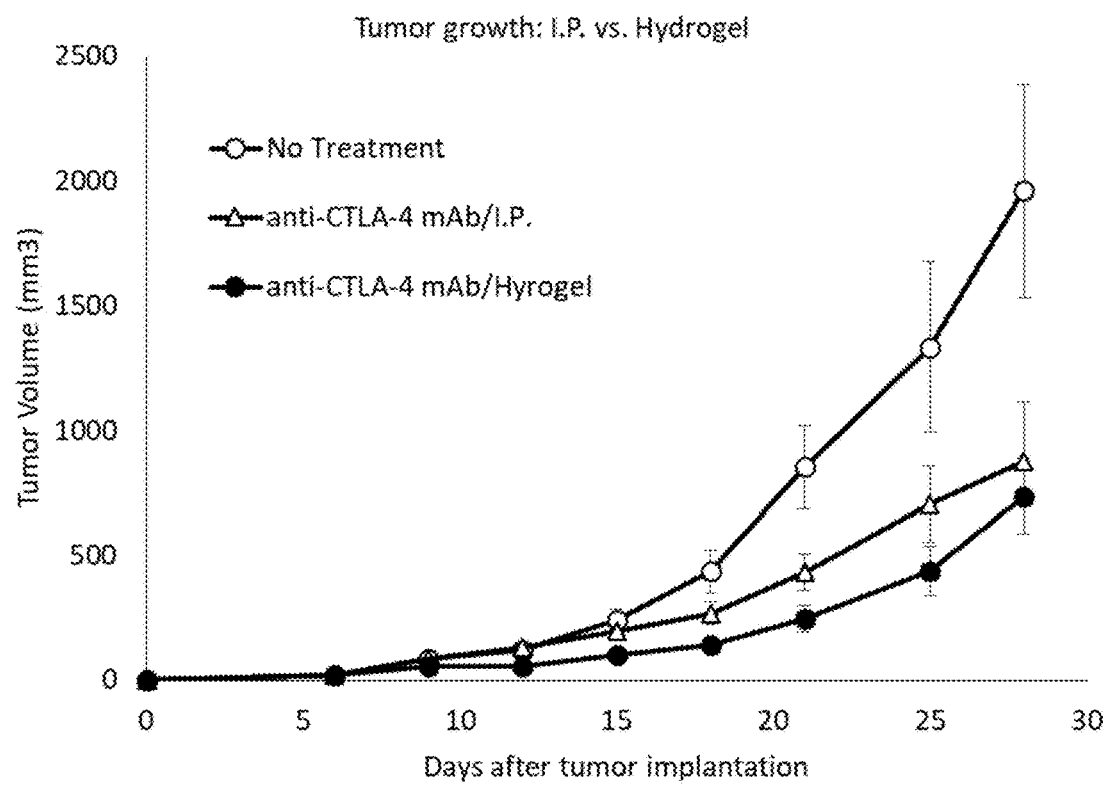
Figure 10C:
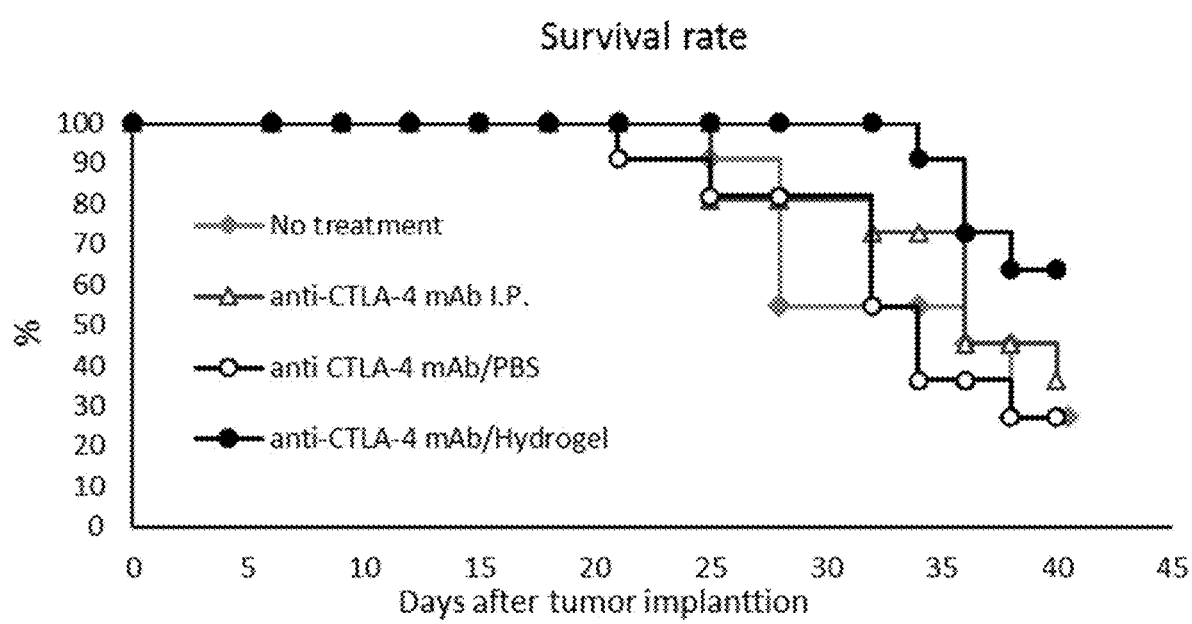

FIGS. 10A-10C: Local administration of anti-CTLA-4 mAb encapsulated in a hydrogel suppresses tumor growth. C57BL/6 mice were implanted with MC-38 cells ($3.5 \times 10^5$) by subcutaneous injection. Treatment was initiated on day 6 following the confirmation of palpable tumor. FIG. 10A: A control group received no additional injections or treatment, a treatment group was injected into the peri-tumoral subcutaneous tissue with anti-CTLA-4 mAb (50 µg) that had been encapsulated within a hydrogel followed by a second dose 5 days later (total dose 100 ug), and a second treatment group was injected into the peri-tumoral subcutaneous tissue with anti-CTLA-4 mAb (50 µg) that had been suspended in PBS (i.e. no hydrogel) followed by a second dose 5 days later (total dose 100 ug). FIG. 10B: A third treatment group, representing a positive control for the effects of systemically-administered anti-CTLA-4, received 200 µanti-CTLA-4 mAb that had been suspended in PBS and administered by intraperitoneal (I.P.) injection with repeat doses on days 9 and 12 (total dose 600 µg). Tumor volume ($mm^3$) was measured every 3-4 days. (11 mice/group. Error bar=Standard Error). FIG. 10C: Survival rates of the four groups were determined over a 40 day period.

DESCRIPTION OF ILLUSTRATIVE EMBODIMENTS

Provided herein are compositions, apparatus and/or methods that include novel functionalized HA-based hydrogels for retaining and releasing protein-based biologic reagents in a time-controlled manner. These and other non-limiting aspects of this disclosure are discussed in further detail in the following sections.

The present inventors demonstrate that the HA-based hydrogels disclosed herein can effectively be used to provide a sustained release of active agents, such as proteins. Using an embodiment of the HA-based hydrogels disclosed herein, the present inventors showed a drastic decreased in the amount of immune checkpoint inhibitor antibody needed to provide a robust antitumor response when compared to a larger systemic dose. Accordingly, the unwanted side effects/toxicity caused by larger administrations of antibodies can be reduced or avoided without compromising on efficacy.

In contrast, the present inventors disclose that a standard Hyaluronic Acid hydrogel does not perform as previously understood. Unfortunately, due to unique characteristics of assays previously used to assess the timed-release characteristics of hydrogels, the outcome data previously produced a false impression of controlled drug release. When assays were repeated by the present inventors it was determined that this was an artifact due to the small volumes of media used in assays and the long intervals between data point collection. Varying the media volume and time intervals results in completely different outcomes which related to the conditions used in the assay and not the intrinsic features of the hydrogels. It was determined that protein loaded into a standard hydrogel is delivered in just a few hours and not over weeks as previously thought.

It was also determined that the poor and variable recovery of proteins from hydrogels that has been reported in the literature is not due to long-term retention within the hydrogel matrix as previously assumed, but due to degradation, denaturation, and/or functional inactivation of the added protein. The present inventors have determined the cause of the denaturation, degradation, and/or functional inactivation as aspects of the hydrogel polymerization process. These aspects can be deleterious, especially when the goal is to encapsulate a protein or other form of biologic agent for controlled delivery in a therapeutic setting. The function of proteins and other complex biologic agents may be highly dependent upon their form, spatial-configuration, and chemical reactivity. The present inventors determined that the same chemical reactions and molecular interactions that are required to promote the cross-linking between hydrogel constituents can readily bind, denature, oxidize, modify or otherwise functionally inactivate incorporated molecules and thereby disrupt the intended biologic response. The present inventors disclose herein methods to protect proteins from denaturation, degradation, and/or functional inactivation. The result is the capacity to efficiently load and release biologically active proteins.

It was also determined that by significantly increasing the amount of cross-linking reagent used when formulating the gel, the pore size can be reduced to the point that it does effectively retain proteins. Not meaning to be bound by theory, it is believe that the capacity to do so is related to the molecular weight and size of the protein. Therefore, one may specifically match the gel composition with appropriately sized proteins. As most proteins are too small on their own, an approach has been developed for using protein conjugates to increase the size of the biologically active proteins while retaining the normal biologic function. Antibodies and conjugates of proteins with antibody sub-units produce optimal sized reagents for some of the gels disclosed herein.

In addition to modifying the size of the biologic protein, it has been determined that a biologically active protein linked to a GST tag protein can be used to control retention and release of the biologically active protein. Not meaning to be bound by theory, it is believed that this increases the size, which may be one factor, but also that the GST protein may directly bind to specific thiol-modified components, such as sulfahydral groups, of the gel and thereby retains the protein through a binding interaction between the GST and the gel. The use of GST-tagged proteins in this manner adds a targeted affinity binding to the gel that can be used to control retention and release of added proteins.

It has also been determined that incorporating hyaluronidase (an enzyme that degrades hyaluronic acid) into the hydrogel, can cause and control the auto-degradation of the gel so that it breaks down and disappears in a controlled manner. By controlling the concentration of hyaluronidase, the gel can be made to dissolve over any pre-specified number of days to weeks. Recombinant human Hyaluronidase has already been approved in the United States by the FDA for subcutaneous injection to facilitate drug delivery and is used as a single injection when placing an intravenous line into the subcutaneous tissue in small children or others who have poor venous access. It has been used in the research lab setting to dissolve hydrogels, but in those cases it is added as an exogenous reagent to the culture media and not incorporated into the gel. This disclosure describes that hyaluronidase can be formulated directly into the gel where it binds to the hyaluronic acid and slowly digests the gel matrix. The degradation provides an approach to control the breakdown of injected hydrogels and to control the release of retained proteins.

A. Functionalized Hyaluronic Acid-Based Hydrogels and Compositions Capable of Forming Such A gel can be a sponge-like, three-dimensional solid network whose pores are filled with another non-gaseous substance, such as a liquid. Hyaluronic acid-based hydrogels (HA-based hydrogels), are gels comprising cross-linked hyaluronic acid. HA-based hydrogels are tissue biocompatible, have the potential to polymerize and transition from a liquid to a solid at the site of injection, and are inherently porous, which provides an opportunity for loading them with other molecules or reagents as a reservoir for local delivery.

The HA-based hydrogels disclosed herein can use natural hyaluronic acid (HA) or functionalized HA. HA may be functionalized by methods known in the art. As non-limiting examples, HA can be functionalized by adding sulfhydryl groups, reacting HA with adipic acid dihydrazide to form adipic acid dihydrazide-derivitized HA (HAADH); by periodate oxidation or hetero-bifunctional reagent containing a protected aldehyde to form aldehyde-functionalized HA (HAALD); functionalized by amidation by homobifunctional reagents containing a divalent disulfide-based protecting group, followed by dithiothreitol (DTT) treatment; and functionalized by adding serine residues to HA and oxidizing to aldehyde groups (Xu et al., 2012). The HA-based hydrogel can comprise any amount of HA or functionalized HA. Concentrations of HA and/or functionalized HA in the HA-based hydrogel may be, but are not limited to greater than 4%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, less than 0.01% w/v, and any range therein. In some embodiments, the HA-based hydrogel contains 0.2% to 1.0% w/v HA and/or functionalized HA. In further embodiments, the HA-based hydrogel contains 0.2% to 0.8% w/v HA and/or functionalized HA. In some instances, the functionalized HA is commercially available. In some instances, the commercially available functionalized HA is thiolated HA. In some instances, the commercially available functionalized HA is from ES Cell International (ESI-BIO™) and/or BioTime, Inc., such as GLYCOSIL®. In some instances, the commercially available functionalized HA is from Vornia Biomaterials, such as Fast-Gelling Thiol-Modified Hyaluronic Acid (HA-SH).

The HA-based hydrogels disclosed herein can be cross-linked by methods known in the art. Cross-linking agents include, but are not limited to polyethylene glycol (PEG), PEG diacrylate (PEGDA), bisepoxide, glutaraldehyde, 1-ethyl-3-(3-dimethylaminopropyl) carbodiimide hydrochloride (EDC), and biscarbodiimid. The HA-based hydrogel can comprise any amount of cross-linking agent. Concentrations of cross-linking agent in the HA-based hydrogel may be, but are not limited to greater than 4%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, less than 0.01% w/v, and any range therein. In some embodiments, the HA-based hydrogel contains 0.1% to 2.0% w/v cross-linking agent. In further embodiments, the HA-based hydrogel contains 0.1% to 1.2% w/v cross-linking agent. In some instances, PEGDA is used as the cross-linking agent. In some instances, PEGDA is commercially available. In some instances, PEGDA is commercially available from Sigma, PolySciences Inc., ES Cell International (ESI-BIO™), and/or BioTime, Inc. In some instances, the PEGDA is commercially available as EXTRALINK® from ES Cell International (ESI-BIO™) and/or BioTime, Inc. The number average molecular weight of PEGDA may be, but is not limited to, greater than 20,000, 15,000, 10,000, 9,000, 8,000, 7,000, 6,000, 5,000, 4,000, 3,000, 2,000, 1,000, 900, 800, 700, 600, 500, 400, 300, 200, 100, less than 100, and any range therein. In some instances, the PEGDA has a number average molecular weight of 3,400. In some instances, PEGDAs of similar molecular weight are expected to act similarly in hydrogel formation.

The HA-based hydrogels disclosed herein can encapsulate, entrap, bind, and/or contain a compound or composition to be delivered. The hydrogel may deliver, but is not limited to, a drug, a biologically active agent, a virus, a bacterial particle, or any deliverable known in the art to be delivered by a hydrogel. The bioactive agent may include, but are not limited to, a protein, a peptide, a fusion protein, a fusion peptide, a conjugated protein, a conjugate peptide, an antibody, a cytokine, etc. Further non-limiting examples include therapeutic antibodies, such as antibodies that target immune check point inhibitors (e.g. target Human Ig, CTLA-4, PD-1, PD-L1), GST tagged proteins, and Fc conjugated proteins such as cytokines. The compound or composition to be delivered can have any molecular weight. The compound or composition to be delivered can have, but is not limited to, a molecular weight of less than, greater than, or about 1000 kD, 1000, 900, 800, 700, 600, 500, 400, 300, 200, 190, 180, 170, 160, 150, 140, 130, 120, 110, 100, 90, 80, 70, 60, 50, 40, 30, 20, 10, 9, 8, 7, 6, 5, 4, 3, 2, 1, 0.9, 0.8, 0.7, 0.6, 0.5, 0.4, 0.3, 0.2, 0.1, less than 0.1 kD, and any range therein. In some embodiments, the HA-based hydrogel contains a compound or composition to be delivered with a molecular weight of 10 kD to 300 kD, 100 kD to 200 kD, 80 kD to 200 kD, 130 kD to 170 kD, 140 kD to 160 kD, about 150 kD, or 150 kD, or any range derivable therein. The HA-based hydrogel can release the compound or composition to be delivered over any period of time. The HA-based hydrogel can release the compound or composition to be delivered over, but not limited to, greater than 100 days, or over the course of 100, 90, 80, 70, 60, 50, 40, 30, 20, 10, 9, 8, 7, 6, 5, 4, 3, 2, 1 days, or less than 1 day(s), or any range therein. In certain embodiments, the HA-based hydrogel can release the compound or composition to be delivered over 1 to 30 days. The compound or composition to be delivered can retain any amount of activity when encapsulated, entrapped, bound, and/or contained by the HA-based hydrogels when compared to the compound or composition to be delivered when not encapsulated, entrapped, bound, and/or contained by HA-based hydrogels. The compound or composition to be delivered when encapsulated, entrapped, bound, and/or contained by the HA-based hydrogels can retain, but are not limited to, about 100%, 90%, 80%, 70%, 60%, 50%, 40%, 30%, 20%, 10%, 9%, 8%, 7%, 6%, 5%, 4%, 3%, 2%, 1%, less than 1%, or any range therein, of activity when compared to the compound or composition to be delivered when not encapsulated, entrapped, bound, and/or contained by HA-based hydrogels. In some embodiments, the compound or composition to be delivered retains 60% of activity. In further embodiments, the compound or composition to be delivered retains 80% of activity.

The HA-based hydrogels disclosed herein can encapsulate, entrap, bind, and/or contain a compound or composition to degrade or depolymerize the HA-based hydrogel. As a non-limiting example, a HA-based hydrogel can contain hyaluronidase as a compound to degrade or depolymerize the HA-based hydrogel. Hyaluronidase may be formulated directly into the gel. Hyaluronidase may be evenly or unevenly dispersed throughout the HA-based hydrogel and/or solubilized throughout the porous cross-linked polymeric matrix and/or in a composition capable of forming a HA-based hydrogel with or without being exposed to an activating agent. In non-limiting examples, hyaluronidase may be recombinant, synthetic, purified from a natural source, a fusion and/or conjugated hyaluronidase, or an enzymatically active truncated hyaluronidase. The HA-based hydrogel can contain any amount of hyaluronidase. Concentrations of hyaluronidase in the HA-based hydrogel may be, but are not limited to greater than 1000 units/ml, 1000, 900, 800, 700, 600, 500, 400, 300, 200, 100, 90, 80, 70, 60, 50, 40, 30, 20, 10, 9, 8, 7, 6, 5, 4, 3, 2, 1, 0.9, 0.8, 0.7, 0.6, 0.5, 0.4, 0.3, 0.2, 0.1 units/ml, or less than 0.1 units/ml, and any range therein. In certain embodiments, the HA-based hydrogel contains 1 to 200 units/ml of hyaluronidase. In additional embodiments, the HA-based hydrogel contains 2 to 100 units/ml of hyaluronidase.

The HA-based hydrogels disclosed herein can contain compounds or compositions to decrease the degradation, denaturation, and/or functional inactivation of a biologically active agent. As non-limiting examples, a HA-based hydrogel can contain hyaluronidase, gelatin, and/or functionalized gelatin. The hyaluronidase, gelatin, and/or functionalized gelatin may be formulated directly into the gel. The hyaluronidase, gelatin, and/or functionalized gelatin can be covalently bound to the hyaluronic acid and/or the cross-linking agent. The hyaluronidase, gelatin, and/or functionalized gelatin may be evenly or unevenly dispersed throughout the HA-based hydrogel and/or solubilized throughout the porous cross-linked polymeric matrix and/or in a composition capable of forming a HA-based hydrogel with or without being exposed to an activating agent. In non-limiting examples, hyaluronidase may be any hyaluronidase described herein or known in the art. In non-limiting examples, gelatin may be hydrolyzed collagen, recombinant, purified from a natural source, a fusion and/or conjugated gelatin, or a truncated gelatin, or any gelatin described herein or known in the art. Gelatin may be functionalized by methods known in the art. As a non-limiting example, gelatin can be functionalized by adding thiol groups, such as in GELIN-S®. In some instances, gelatin or functionalized gelatin is commercially available. In some instances, the commercially available functionalized gelatin is a thiol-modified gelatin. In some instances, the commercially available thiol-modified gelatin is from ES Cell International (ESI-BIO™) and/or BioTime, Inc. such as GELIN-S®. In some instances, the commercially available thiol-modified gelatin is from Vornia Biomaterials, such as Thiolated Gelatin (Gel-SH). The HA-based hydrogel can comprise any amount of hyaluronidase described herein. The HA-based hydrogel can comprise any amount of gelatin and/or functionalized gelatin. Concentrations of gelatin and/or functionalized gelatin in the HA-based hydrogel may be, but are not limited to, less than about, greater than about, or equal to about 4%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% w/v, or less than 0.01% w/v, or any range therein. In some embodiments, the HA-based hydrogel contains 0.1% to 0.8% w/v gelatin and/or functionalized gelatin. In additional embodiments, the HA-based hydrogel contains 0.2% to 0.6% w/v gelatin and/or functionalized gelatin. The HA-based hydrogel can decrease the degradation, denaturation, and/or functional inactivation of a biologically active agent by any amount. The decrease in degradation, denaturation, and/or functional inactivation may slow the decrease of the activity of the biologically active agent by any amount. The amount of activity a biologically active agent does not decrease when compared to the activity of the biological agent that has not been incorporated into a HA-based hydrogel disclosed herein may be, but is not limited to, more than 80%, 70%, 60%, 50%, 40%, 30%, 20%, 10%, 5%, 4%, 3%, 2%, 1%, less than 1%, or any range therein. In some cases, the activity of the biologically active agent does not decrease by more than 40%. In other embodiments, the activity of the biologically active agent does not decrease by more than 20%.

Compositions can be prepared that are capable of forming a HA-based hydrogel. The compositions may contain all or some of the ingredients combined that are required to form a solid HA-based hydrogel disclosed herein and may form a gel when exposed to a gelling agent. The gelling agent may be a compound, an electromagnetic wave including visible and UV light, a cross linker, or may be a condition, such as a temperature or a pH.

B. Methods of Making Hyaluronic Acid-Based Hydrogels and Compositions Capable of Forming Such The HA-based hydrogels disclosed herein can be made by similar methods known in the art for creating other HA-based hydrogels. As a non-limiting example, the HA-based hydrogels can be prepared by the following procedure (see FIG. 7).

Reagent Preparation: As non-limiting examples, the following reagents can be prepared to be used in a composition capable of creating an embodiment of the HA-based hydrogels disclosed herein.

Biologically active agent (Reagent A)—Reagent A can be prepared as a solution or as a reagent that can be dispersed within a solution. The reagent can be prepared at any temperature conducive to retaining the activity of the biologically active agent. Reagent A can be, but is not limited to being, prepared as a solution at room temperature by adding a liquid such as saline or PBS to the biologically active agent, which may be, but is not limited to, a lyophilized powdered biologically active agent. In a non-limiting embodiment, the biologically active agent has (a) a linker group, such as, a glutathione-S-transferase (GST) tag and/or (b) a molecular weight of 10 kD to 300 kD, 100 kD to 200 kD, 80 kD to 200 kD, 130 kD to 170 kD, 140 kD to 160 kD, about 150 kD, or 150 kD, or any range derivable therein.

Optional hyaluronidase component (Reagent B)—Reagent B can be prepared as a solution or as a hyaluronidase reagent that can be dispersed within a solution. The reagent can be prepared at any temperature conducive to retaining the activity of the hyaluronidase. Reagent B can be, but is not limited to being, prepared as a solution by adding a liquid such as saline or PBS to hyaluronidase. Reagent B can be used when producing a self-resorption hydrogel. In a non-limiting embodiment, the reagent is prepared to a concentration of about 1 unit/ml to 200 units/ml, including 2 units/ml to 100 units/ml, in the final HA-based hydrogel solution.

Cross-linking agent (Reagent C)—Reagent C can be prepared as a solution or as a cross-linking reagent that can be dispersed within a solution. The reagent can be prepared at any temperature conducive to retaining the activity of the cross-linking agent. Reagent C can be, but is not limited to being, prepared as a solution by adding a liquid such as water to the cross-linking agent, that can be, but is not limited to, a lyophilized powder cross-linking agent. The reagent can be incubated and mixed at room temperature until the solution is clear. In a non-limiting embodiment, the reagent is prepared to a concentration of about 0.2% w/v to 2.0% w/v, or of about 0.1% w/v to 1.2% w/v, in the final HA-based hydrogel solution.

HA or functionalized HA component (Reagent D)—Reagent D can be prepared as a solution or as a component that can be dispersed within a solution. The reagent can be prepared at any temperature conducive to retaining the reactivity of HA for cross-linking. Reagent D can be, but is not limited to being, prepared as a solution by adding a liquid such as water to the HA or functionalized HA, which can be, but is not limited to, a lyophilized powder HA or functionalized HA. The solution can be incubated and mixed at room temperature or 37° C. for 30 to 60 minutes until the solution is clear. In a non-limiting embodiment, the reagent is prepared to a concentration of about 0.2% w/v to 1.0% w/v, including 0.2% w/v to 0.8% w/v, in the final HA-based hydrogel solution.

Optional gelatin component (Reagent E)—Reagent E can be prepared as a solution or as a component that can be dispersed within a solution. The reagent can be prepared at any temperature conducive to retaining the gelling activity and/or functional inactivation inhibiting activity of the gelatin. Reagent E can be, but is not limited to being, prepared as a solution by adding a liquid such as water to the gelatin, which can be, but is not limited to, a lyophilized powder gelatin. The solution can be incubated and mixed at room temperature or 37° C. for 30 to 60 minutes until the solution is clear. Reagent E can be used when producing a gelatin-containing HA-based hydrogel. In a non-limiting embodiment, the reagent is prepared to a concentration of about 0.1% w/v to 0.8% w/v, including such as about 0.2% w/v to 0.6% w/v, in the final HA-based hydrogel solution.

Solution Preparation: As non-limiting examples, the following solutions can be prepared to be used in a composition capable of creating an embodiment of the HA-based hydrogels disclosed herein.

Solution I—Mix or evenly disperse Reagent A and optionally Reagent B together to produce Solution I. This is done, for example, at room temperature and using solutions of Reagent A and optionally Reagent B.

Solution II—Mix or evenly disperse Solution I and Reagent C to produce Solution II. This is done, for example, at room temperature and using a solution of Reagent C.

Solution III—Mix or evenly disperse Reagent D and optionally Reagent E together to produce Solution III. This is done, for example, at room temperature and incubate for 10-30 min using solutions of Reagent D and optionally Reagent E.

The solutions and reagents above may be stored for later use, combined as a kit of any combination of separate solutions/reagents, or used in the proceeding step to prepare a final HA-based hydrogel solution.

Prepare final HA-based hydrogel solution—Mix Solution II and Solution III together to produce the final HA-based hydrogel solution. This is done, for example, at room temperature for 3-40 min.

A HA-based hydrogel with self-absorbing characteristics is produced when Reagent B is included. A HA/Gelatin Hydrogel is produced when Reagent E is included. A HA/Gelatin Hydrogel with self-absorbing characteristics is produced when both Reagent B and Reagent E are included.

Activation: The final HA-based hydrogel solution can be solidified by any means known in the art to activate the cross-linking reaction, or can form a solid without the need for an additional activation step. In some embodiments, the solution begins to solidify to form a HA-based hydrogel when the HA or functionalized HA is mixed with a cross-linker. The rate of solidification can be controlled by the concentration of the reagents in the final HA-based hydrogel solution or the manner in which the cross-linking reaction is activated.

Administration: The final HA-based hydrogel solution can be administered to a subject as a solution or after it has solidified. The final HA-based hydrogel solution can be allowed to solidify and used for the uses contemplated and disclosed herein, and any use that HA-based hydrogels known in the art are used or contemplated to be used. The final HA-based hydrogel solution can be administered prior to the solidification of the hydrogel. The final HA-based hydrogel solution or a solidified HA-based hydrogel can be administer by any means known or contemplated in the art for other HA-based hydrogel solutions and/or solidified hydrogels. In one embodiment, the final HA-based hydrogel solution is injected into or at the desired tissue/organ location of the subject prior to hydrogel solidification and the solution subsequently solidifies in or at the desired tissue/organ location. The final HA-based hydrogel solution can be parentally injected. Parentally injection includes injection into subcutaneous, intramuscular, or intradermal regions. The final HA-based hydrogel solution or a solidified HA-based hydrogel can be topically applied or surgically implanted.

Kits that include the compositions of the present invention are also contemplated. In certain embodiments, the composition is comprised in a container. The container can be, but is not limited to, a bottle, dispenser, or package. In some aspects, the container can dispense a pre-determined amount of the composition. In certain aspects, the compositions is dispensed in a spray, mist, dollop, or liquid. The container can include indicia on its surface. The indicia can be a word, an abbreviation, a picture, or a symbol. The kit can contain instructions, such as instructions containing direction regarding a method of making a HA-based hydrogel disclosed herein.

C. Methods of Using a Hyaluronic Acid-based Hydrogel or Composition Disclosed Herein The hyaluronic acid-based hydrogel or composition disclosed herein can be used in a method to treat a subject. The cancers amenable for treatment include, but are not limited to, tumors of all types, locations, sizes, and characteristics. The methods and compositions of the disclosure are suitable for treating, for example, pancreatic cancer, colon cancer, acute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, lymphoid cancer, bronchial adenomas/carcinoids, tracheal cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal germ cell tumor, extrahepatic bile duct cancer, eye cancer, intraocular melanoma eye cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), non-small cell lung cancer, small cell lung cancer, lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, melanoma, merkel cell carcinoma, adult malignant mesothelioma, childhood mesothelioma, metastatic squamous neck cancer, mouth cancer, multiple endocrine neoplasia syndrome, multiple myeloma/ plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian cancer, ovarian epithelial cancer (surface epithelial-stromal tumor), ovarian germ cell tumor, ovarian low malignant potential tumor, pancreatic cancer, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, childhood Salivary gland cancer Sarcoma, Ewing family of tumors, Kaposi sarcoma, soft tissue sarcoma, uterine sezary syndrome sarcoma, skin cancer (nonmelanoma), skin cancer (melanoma), skin carcinoma, Merkel cell small cell lung cancer, small intestine cancer, soft tissue sarcoma, squamous cell carcinoma. squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).The tumor can be a solid tumor and/or metastatic. In some embodiments, the patient has been previously treated for the cancer. In some embodiments, the subject was resistant to the previous cancer treatment. In some embodiments, the subject was determined to be a poor responder to the cancer treatment.

The hyaluronic acid-based hydrogel or composition disclosed herein can contain one or more biologically active agent(s) effective against a cancer. The hyaluronic acid-based hydrogel or composition disclosed herein can be administered with one or more of a second embodiment of a hyaluronic acid-based hydrogel or composition disclosed herein containing one or more biologically active agent(s). The hyaluronic acid-based hydrogel or composition disclosed herein can be administered with one or more biologically active agent(s) and/or therapies that are not contained in a hyaluronic acid-based hydrogel or composition disclosed herein.

a. Checkpoint Inhibitor(s)

The bioactive agent(s) can be one or more immune checkpoint inhibitor(s). An "immune checkpoint inhibitor" is any molecule that directly or indirectly inhibits, partially or completely, an immune checkpoint pathway. Without wishing to be bound by any particular theory, it is generally thought that immune checkpoint pathways function to turn on or off aspects of the immune system, particularly T cells. Following activation of a T cell, a number of inhibitory receptors can be upregulated and present on the surface of the T cell in order to suppress the immune response at the appropriate time. In the case of persistent immune stimulation, immune checkpoint pathways can suppress the immune response and lead to immune exhaustion. Examples of immune checkpoint pathways include, without limitation, PD-1/PD-L1, CTLA4/B7-1, TIM-3, LAGS, By-He, H4, HAVCR2, ID01, CD276 and VTCN1. In the instance of the PD-1/PD-L1 immune checkpoint pathway, an inhibitor may bind to PD-1 or to PD-L1 and prevent interaction between the receptor and ligand. Therefore, the inhibitor may be an anti-PD-1 antibody or anti-PD-L1 antibody. Similarly, in the instance of the CTLA4/B7-1 immune checkpoint pathway, an inhibitor may bind to CTLA4 or to B7-1 and prevent interaction between the receptor and ligand. Further examples of immune checkpoint inhibitors can be found, for example, in WO2014/144885. Such immune checkpoint inhibitors are incorporated by reference herein. In some embodiments of any one of the methods, compositions or kits provided, the immune checkpoint inhibitor is a small molecule inhibitor of an immune checkpoint pathway. In some embodiments of any one of the methods, compositions or kits provided, the immune checkpoint inhibitor is a polypeptide that inhibits an immune checkpoint pathway. In some embodiments of any one of the methods, compositions or kits provided, the inhibitor is a fusion protein. In some embodiments of any one of the methods, compositions or kits provided, the immune checkpoint inhibitor is an antibody. In some embodiments of any one of the methods, compositions or kits provided, the antibody is a monoclonal antibody.

Non-limiting examples of immune checkpoint inhibitors include fully human monoclonal antibodies, such as RG7446, BMS-936558/MDX-1106, BMS-936559 (anti-PD-L1 antibody), Yervoy/ipilimumab (anti-CTLA-4 checkpoint inhibitor), and Tremelimumab (CTLA-4 blocking antibody); humanized antibodies, such as pidilizumab (CT-011, CureTech Ltd.) and lambrolizumab (MK-3475, Merck, PD-1 blocker); and fusion proteins, such as AMP-224 (Merck). Other examples of checkpoint inhibitors include anti-OX40, PD-L1 monoclonal Antibody (Anti-B7-H1; MEDI4736), Nivolumab (BMS-936558, Bristol-Myers Squibb, anti-PD-1 antibody), CT-011 (anti-PD-1 antibody), BY55 monoclonal antibody, MPLDL3280A (anti-PD-L1 antibody), and MSB0010718C (anti-PD-L1 antibody), MDX-1105 (Medarex), MPDL3280A (Genentech), Anti-KIR antibodies such as lirlumab (Innate Pharma) and IPH2101 (Innate Pharma) may perform similar functions in NK cells. Further examples of checkpoint inhibitors include agonistic anti-4-1bb antibody; agonistic anti-CD27 antibody; agonistic anti-GTIR antibody; agonistic anti-OX40 antibody; and antagonistic anti-TIM3 antibody.

b. Antibodies and Antibody Like Molecules

The bioactive agent(s) can be an antibody. The antibody can be an antibody or an antibody like molecule. These antibodies may be used in various compositions, kits, etc., and/or diagnostic or therapeutic applications described herein.

An antibody can be any immunologic binding agent such as IgG, IgM, IgA, IgD and IgE as well as polypeptides comprising antibody CDR domains that retain antigen binding activity. Thus, an antibody can be any antibody-like molecule that has an antigen binding region, and includes antibody fragments such as Fab', Fab, F(ab')$_2$, single domain antibodies (DABs), Fv, scFv (single chain Fv), and polypeptides with antibody CDRs, scaffolding domains that display the CDRs (e.g., anticalins) or a nanobody. For example, the nanobody can be antigen-specific VHH (e.g., a recombinant VHH) from a camelid IgG2 or IgG3, or a CDR-displaying frame from such camelid Ig. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with embodiments. Minibodies are sFv polypeptide chains which include oligomerization domains at their C-termini, separated from the sFv by a hinge region (Pack et al., Biochem., 31:1579-1584, 1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art (see, e.g., Pack et al., Biochem., 31:1579-1584, 1992; Cumber et al., J. Immunology, 149B:120-126, 1992).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods (Liu et al. Cell Mol. Biol., 49(2):209-216, 2003).

Alternative scaffolds for antigen binding peptides, such as CDRs are also available and can be used to generate antigen-binding molecules in accordance with the embodiments. Generally, a person skilled in the art knows how to determine the type of protein scaffold on which to graft at least one of the CDRs arising from the original antibody. More particularly, it is known that to be selected, such scaffolds must meet the greatest number of criteria as follows (Skerra, J. Mol. Recogn., 13:167-187, 2000): good phylogenetic conservation; known three-dimensional structure (as, for example, by crystallography, NMR spectroscopy or any other technique known to a person skilled in the art): small size: few or no post-transcriptional modifications; and/or easy to produce, express and purify.

The origin of such protein scaffolds can be, but is not limited to, the structures selected among: fibronectin and preferentially fibronectin type 111 domain 10, lipocalin, anticalin (Skerra, 2001), protein Z arising from domain B of protein A of Staphylococcus aureus, thioredoxin A or proteins with a repeated motif such as the "ankyrin repeat" (Kohl et al., Proc. Natl. Acad. Sci., USA, 100(4):1700-1705, 2003), the "armadillo repeat", the "leucine-rich repeat" and the "tetratricopeptide repeat". For example, anticalins or lipocalin derivatives are a type of binding proteins that have affinities and specificities for various target molecules and can be used as antigen binding molecules. Some example proteins are described in US Patent Publication Nos. 20100285564, 20060058510, 20060088908, 20050106660, and PCT Publication No. WO2006/056464, incorporated herein by reference.

Scaffolds derived from toxins such as, for example, toxins from scorpions, insects, plants, mollusks, etc., and the protein inhibiters of neuronal NO synthase (PIN) may also be used in certain aspects.

Monoclonal antibodies (MAbs) are recognized to have certain advantages, e.g., reproducibility and large-scale production. Embodiments include monoclonal antibodies of the human, murine, monkey, rat, hamster, rabbit and chicken origin.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin can be an immunoglobulin comprising a human framework region and one or more CDR's from a non-human (usually a mouse or rat) immunoglobulin. The non-human immunoglobulin providing the CDR's can be called the "donor" and the human immunoglobulin providing the framework can be called the "acceptor". A "humanized antibody" can be an antibody comprising a humanized light chain and a humanized heavy chain immunoglobulin.

c. Chemotherapeutic Agent

The bioactive agent(s) can be a chemotherapeutic agent. The term "chemotherapeutic agent," refers to a therapeutic compound and/or drug which may be used to, among other things, treat cancer. For example, a chemotherapeutic agent may include, but is not limited to, any agent that interferes with cell division, disrupts normal functionality of microtubules, inhibits utilization of a metabolite, substitutes nucleotide analogs into cellular DNA, or inhibits enzymes necessary for DNA replication.

Suitable classes of chemotherapeutic agents include (a) Alkylating Agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, lomustine, chlorozoticin, streptozocin) and triazines (e.g., dicarbazine), (b)

Antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), (c) Natural Products, such as vinca alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-α), and (d) Miscellaneous Agents, such as platinum coordination complexes (e.g., cisplatin, carboplatin), substituted ureas (e.g., hydroxyurea), methylhydiazine derivatives (e.g., procarbazine), and adreocortical suppressants (e.g., taxol and mitotane).

The amount of the chemotherapeutic agent delivered to the patient may be variable. In one suitable embodiment, the chemotherapeutic agent may be administered in an amount effective to cause arrest or regression of the cancer in a host, when the chemotherapy is administered contained in and/or with the hyaluronic acid-based hydrogel or composition disclosed herein. In other embodiments, the chemotherapeutic agent may be administered in an amount that is anywhere between 2 to 10,000 fold less than the chemotherapeutic effective dose of the chemotherapeutic agent required if the agent were administered systemically or not encapsulated in a hydrogel disclosed herein. For example, the chemotherapeutic agent may be administered in an amount that is about 20 fold less, about 500 fold less or even about 5000 fold less than the chemotherapeutic effective dose of the chemotherapeutic agent when delivered systemically. The chemotherapeutics of the disclosure can be tested in vivo for the desired therapeutic activity in combination with the hyaluronic acid-based hydrogel or composition disclosed herein, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

Actual dosage levels of the active ingredients in the methods of this disclosure may be varied so as to obtain an amount of the active ingredient which is effective to achieve the desired therapeutic response for a particular patient, composition and mode of administration, without being toxic to the patient. The selected dosage level will depend upon a variety of factors, including the activity of the chemotherapeutic agent selected, the route of administration, the time of administration, the rate of excretion of the chemotherapeutic agent, the duration of the treatment, other drugs, compounds and/or materials used in combination with the particular chemotherapeutic agent, the age, sex, weight, condition, general health and prior medical history of the patient being treated, and like factors well known in the medical arts.

d. Ionizing Radiation

As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

The amount of ionizing radiation needed in a given cell depends inter alia upon the nature of that cell. Means for determining an effective expression inducing amount are well known in the art.

In some embodiments, the amount of ionizing radiation is greater than 20 Gray and is administered in one dose. In some embodiments, the amount of ionizing radiation is 18 Gy and is administered in three doses. In some embodiments, the amount of ionizing radiation is at least, at most, or exactly 2, 4, 6, 8, 10, 15, 16, 17, 18, 19, 20, 21, 22, 23, 24, 25, 26, 27, 18, 19, 30, 31, 32, 33, 34, 35, 36, 37, 38, 39, 40, 41, 42, 43, 44, 45, 46, 47, 48, 49, or 40 Gy (or any derivable range therein). In some embodiments, the ionizing radiation is administered in at least, at most, or exactly 1, 2, 3, 4, 5, 6, 7, 8, 9, or 10 does (or any derivable range therein). When more than one dose is administered, the does may be about 1, 4, 8, 12, or 24 hours or 1, 2, 3, 4, 5, 6, 7, or 8 days or 1, 2, 3, 4, 5, 6, 7, 8, 9, 10, 12, 14, or 16 weeks apart, or any derivable range therein.

In some embodiments, the amount of IR may be presented as a total dose of IR, which is then administered in fractionated doses. For example, in some embodiments, the total dose is 50 Gy administered in 10 fractionated doses of 5 Gy each. In some embodiments, the total dose is 50-90 Gy, administered in 20-60 fractionated doses of 2-3 Gy each. In some embodiments, the total dose of IR is at least, at most, or about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, or 150 (or any derivable range therein). In some embodiments, the total dose is administered in fractionated doses of at least, at most, or exactly 1, 2, 3, 4, 5, 6, 7, 8, 9, 10, 12, 14, 15, 20, 25, 30, 35, 40, 45, or 50 Gy (or any derivable range therein). In some embodiments, at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 fractionated doses are administered (or any derivable range therein). In some embodiments, at least, at most, or exactly 1, 2, 3, 4, 5, 6, 7, 8, 9, 10, 11, or 12 (or any derivable range therein) fractionated doses are administered per day. In some embodiments, at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) fractionated doses are administered per week.

In some embodiments, the total dose of IR is at least 50 Gy. In some embodiments, the IR is administered in 5-15 fractionated doses. In some embodiments, the IR is administered in 10 fractionated doses. In some embodiments, the total dose of IR is 20-120 Gy. In some embodiments, the total dose of IR is 50-90 Gy. In some embodiments, the IR is administered in fractionated doses of 2-3 Gy. In some embodiments, three to seven fractionated doses are administered in a week. In some embodiments, one fractionated dose of 2-3 Gy is administered per day for two to eight weeks.

In some embodiments, an IR regimen and/or total IR dose is prescribed by a doctor or attending medical professional. The medical professional may monitor and/or access the progress of the patient throughout the administration of the IR and/or the medical professional may access the patient at the completion of the administration of the prescribed IR dose and prescribe a new dose/regimen of IR based on the assessment.

e. Combination Therapy

The hyaluronic acid-based hydrogel or composition disclosed herein and related methods of the present disclosure, may also be used in combination with the administration of additional therapies such as the additional therapeutics described herein or in combination with other traditional therapeutics known in the art.

The therapeutic compositions and treatments disclosed herein may precede, be co-current with, and/or follow another treatment or agent by intervals ranging from minutes to weeks. In embodiments where agents are applied separately to a cell, tissue or organism, one would generally ensure that a significant period of time did not expire between the time of each delivery, such that the therapeutic agents would still be able to exert an advantageously combined effect on the cell, tissue or organism. For example, in such instances, it is contemplated that one may contact the cell, tissue or organism with two, three, four or more agents or treatments substantially simultaneously (i.e., within less than about a minute). In other aspects, one or more therapeutic agents or treatments may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering another therapeutic agent or treatment.

Various combination regimens of the therapeutic agents and treatments may be employed. Non-limiting examples of such combinations are shown below, wherein a therapeutic agent such as a composition disclosed herein is "A" and a second agent, such as an additional agent, chemotherapeutic, checkpoint inhibitor, or hyaluronic acid-based hydrogel or composition described herein or known in the art is "B":

| | | | | | | |
|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

In some embodiments, more than one course of therapy may be employed. It is contemplated that multiple courses may be implemented.

EXAMPLES

The following examples are included to demonstrate preferred embodiments of the invention. It should be appreciated by those of skill in the art that the techniques disclosed in the examples which follow represent techniques determined by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Limitations of Standard HA-Based Hydrogel Formulations

It has been determined and disclosed herein that standard HA-based hydrogel formulations do not work as previously described. Assay conditions previously employed for assessing protein retention and release in vitro may have led to erroneous conclusions regarding the capacity for slowly releasing proteins over time.

It has been asserted that HA-based hydrogels can be loaded with an exogenous protein payload and then slowly released over a period of several weeks to months when studied under in vitro conditions (Peattie et al. 2008; Pike et al. 2006). In order to confirm these retention and release characteristics, a commercial HA-based hydrogel (Hystem-C Hydrogel, BioTime, Inc) was prepared and loaded with recombinant human granulocyte macrophage-colony stimulating factor (GM-CSF). Release of the GM-CSF payload into test media was measured over time under in vitro conditions in a standardized manner (see FIG. 1 for details). In brief, the hydrogel constituents were admixed and replicate volumes (0.125 ml) placed into the bottom of culture tubes. After allowing the initial phase of gelation to occur (30 min), either 0.125 ml or 1 ml of release media were added to each tube. Tubes were incubated at 37° C. for 7 days. At designated time points, the release media was collected and replaced with the same volume of fresh media. GM-CSF concentration in the recovered media was assessed by a specific ELISA assay according to the manufacturer's protocol (Biolegend Technical data sheet LEGEND MAX™ Human GM-CSF ELISA Kit with Pre-coated Plates). In order to assess whether any retained GM-CSF remained as "trapped" within the hydrogel matrix at the end of the incubation, hyaluronidase was added for the last 24 hours and the hydrogels were completely digested prior to collecting the final aliquot.

Figure 1:
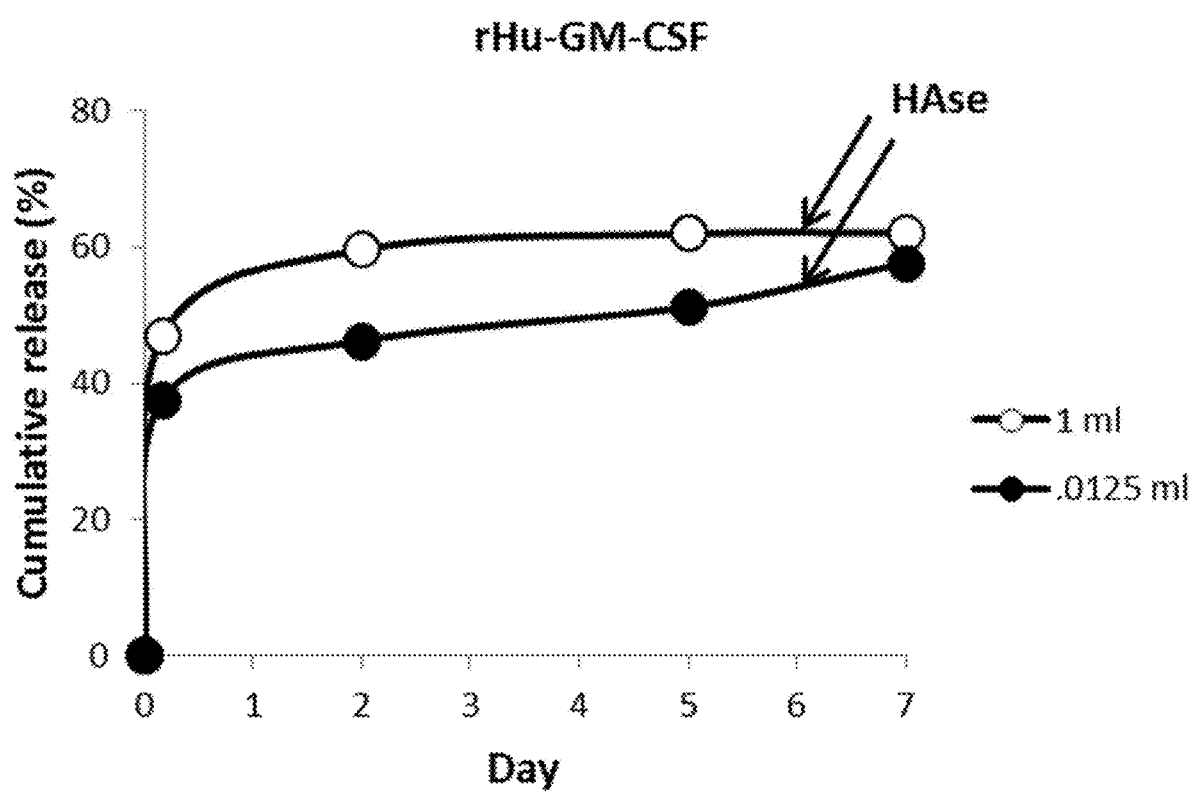
FIG. 1: The volume of the release media utilized in hydrogel release assays can modify the perceived rate of release of an incorporated cytokine, such as granulocyte macrophage-colony stimulating factor (GM-CSF). Recombinant human GM-CSF (5ug) was incorporated into a commercially available HYSTEM-C™ hydrogel using the manufacturer's recommended formulation (GLYCOSIL® [0.4% w/v], GELIN-S® [0.4% w/v], EXTRALINK® [0.2% w/v]). Release media, with a volume of either 0.125 ml or 1 ml was added to replicate culture tubes 30 min after initiating gelation. Media was collected and replaced with fresh media at indicated time points. An exogenous source of hyaluronidase (HAse) (1000 units) was added to the culture at day 6 to lyse the hydrogels before the last collection of media at day 7. Levels of GM-CSF released into the media that was collected at the indicated time points were determined by standard ELISA.

As shown in FIG. 1, the release characteristics for GM-CSF were found to depend upon the volume of release media employed. When a volume of only 0.125 ml of release media was added there appeared to be a sustained release that occurred over time with residual cytokine recovered after the addition of hyaluronidase. However, simply increasing the volume of the release media to 1.0 ml resulted in a much more rapid release with 96.2% of maximum release occurring by the second time point and no additional cytokine recovered after the addition of hyaluronidase. Repeating assays with different volumes and with different time intervals (data not shown) revealed that there was actually very rapid equilibrium between the concentration of cytokine in the gel and that in the release media —occurring within minutes. The shape of the release curve was entirely dependent upon the volume of release media and the number of media exchanges, but not upon the time interval between exchanges. The fraction of recovered cytokine, as a percent of that remaining in the gel, represented a constant fraction at each media exchange. When smaller media volumes or exchanges were used it would appear that the release was slower. When the interval between exchanges was increased it would appear that the release was occurring more slowly.

However, as noted, these features previously attributed to the HA-based hydrogels were primarily driven by the assay conditions and not the protein retention characteristics of the gel. These studies demonstrated that the commercial formulation of HA hydrogel tested would not act as a slow release reservoir for protein reagents in the manner previously suggested by the literature (Cal S et al. 2005; Peattie et al. 2008).

Example 2. Promoters of Chemical Polymerization Process Denature/Degrade Added Proteins In the initial controlled-release experiments (FIG. 1), only a fraction of the loaded GM-CSF protein could be recovered from the hydrogel when measured by ELISA. Further, this fraction was relatively constant for any given protein but varied between different protein factors (for example, the recovery of IL-4 was much less than that of GM-CSF). This feature had been previously noted but not adequately explained (Peattie et al. 2008; Pike et al. 2006). The leading hypothesis was that protein remained within the hydrogel and could not be recovered (Peattie et al. 2008; Pike et al. 2006). However, as demonstrated herein, digestion of the gel with hyaluronidase failed to recover the missing cytokine. Not wishing to be bound be theory, it is believed that reactive components of the hydrogel involved in the gelation reaction might actually denature/destroy/functionally inactivate added protein, rendering it undetectable by ELISA assay.

Figure 2A:
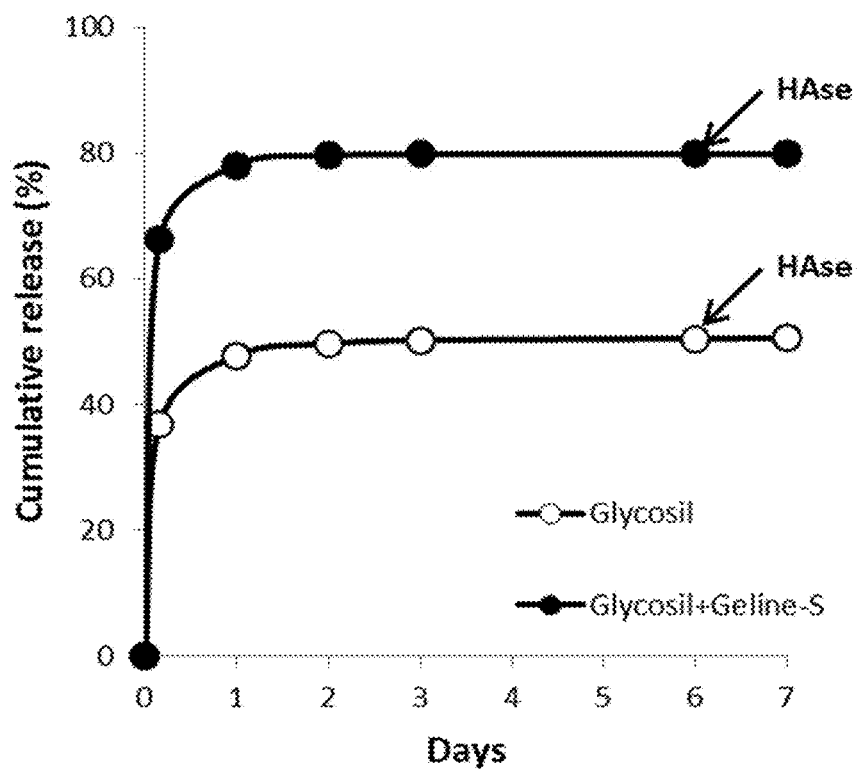
FIGS. 2A-2D.

Hydrogels generally require a specific chemical reaction between the component reagents in order to propagate the matrix structure and the gelation process. For the commercial Hystem C Hydrogel tested in our studies, the hyaluronic acid (GLYCOSIL®, BioTime, Inc.) is functionalized by adding reactive sulfhydryl groups that chemically react under oxidizing conditions when exposed to the Polyethylene (glycol) Diacrylate (PEGDA; EXTRALINK®™, BioTime, Inc.) cross-linking reagent. The Hystem-C formulation also incorporates what is described as an inert filler, thiol-modified gelatin (GELIN-S®), which competes with the GLYCOSIL® and EXTRALINK®™ with respect to forming chemical bonds to the matrix structure. GELIN-S® has been described as a component that promotes better release of added proteins (Peattie et al. 2008; Pike et al. 2006). As a first step in understanding the dynamic interaction between hydrogel components the retention and release characteristics were compared of the HA-based hydrogel when formulated in the presence or absence of GELIN-S® (FIG. 2A). As had been reported in the literature, the retention and release characteristics of the hydrogel were different in the presence of GELIN-S® and its presence was associated with a greater overall GM-CSF protein recovery. However, its presence had no impact on the pattern of release from the hydrogel. On average, the GLYCOSIL®-only hydrogel released 50.6% of the added GM-CSF while the GLYCOSIL®+GELIN-S® hydrogel released 79.9% of loaded GM-CSF. This difference was entirely accounted for by the difference in recovery at the first media exchange at 4 hrs. All release assays were performed with an 8-10 fold excess of release media (as compared to gel volume) to assure that the volume of the release media was not a significant limiting factor (as shown in FIG. 1). Furthermore, the addition of hyaluronidase prior to the final assay time point assured that GM-CSF was not simply captured within the hydrogel matrix structure. Not wishing to be bound by theory, it is believed that the addition of GELIN-S® protected added protein from being denatured, destroyed, and/or functionally inactivated. GM-CSF, as is the case with most protein reagents, contains disulfide bonds that might be particularly susceptible to the chemical cross-linking reactions that take place during the gelation process.

Figure 2B:
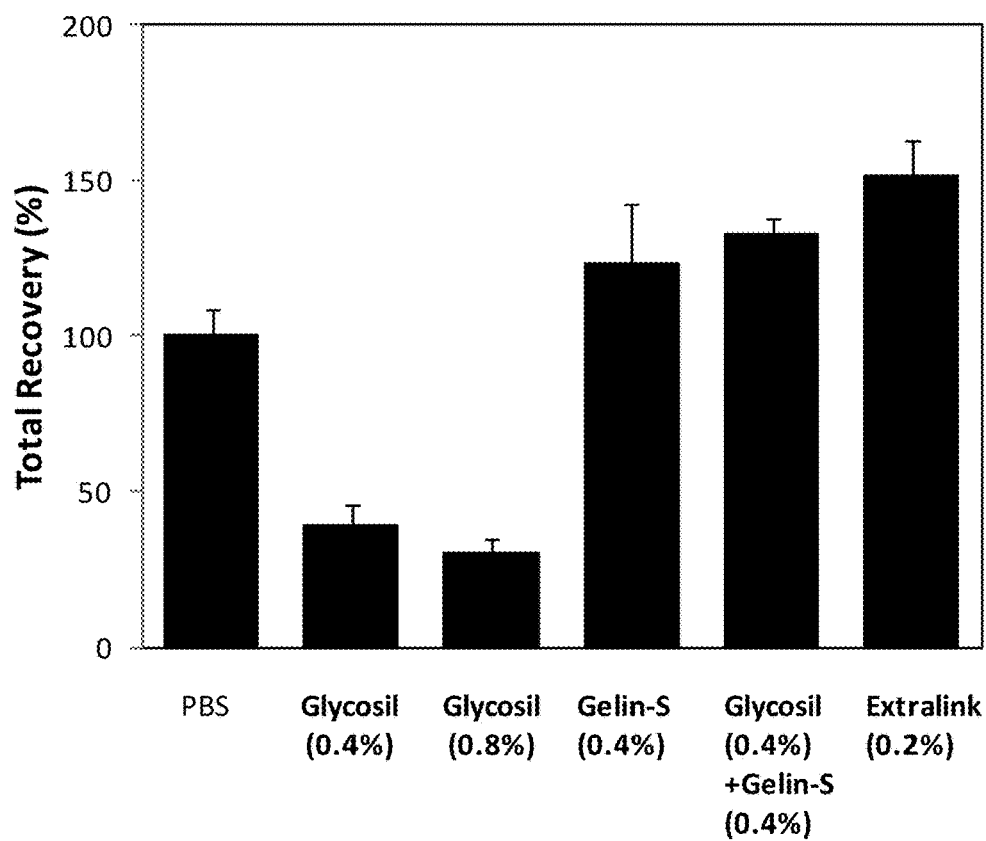

To further investigate the hypothesis, the individual components of the hydrogel formulation were co-cultured, either alone or in combination, with GM-CSF to determine the impact on recoverable protein. As shown in FIG. 2B, co-culture with GLYCOSIL® produced a concentration-dependent reduction in the level of recovered GM-CSF after a 4 hr incubation. Note that 0.4% w/v of GLYCOSIL® represents the same concentration of GLYCOSIL® within the GLYCOSIL®+GELIN-S® hydrogel formulation while the 0.8% w/v of GLYCOSIL® represents the same concentration that is employed in the GLYCOSIL® only hydrogel. The recovery of GM-CSF, when compared to control incubation in PBS alone, was reduced to 39.2% by the 0.4% w/v concentration and to 30.3% by the 0.8% w/v concentration of GLYCOSIL®. In contrast, 123.4% of the GM-CSF present in the PBS control tube was measured when GM-CSF was co-cultured with the GELIN-S® component alone. More importantly, when both GLYCOSIL® and GELIN-S® were co-cultured together with GM-CSF, as occurs in the GLYCOSIL®+GELIN-S® hydrogel, the toxic effects of the GLYCOSIL® were ameliorated. Meanwhile, co-culture of GM-CSF with EXTRALINK® alone showed the highest recovery level of 151.8%, suggesting active protection of GM-CSF from denaturation, degradation, and/or retention within the culture tube. These results identified GLYCOSIL® (thiolated HA) as the only component in Hystem-C hydrogel that reduced the level of recoverable protein and that the presence of GELIN-S® and EXTRALINK® help protect from protein loss, consistent with the observations presented in FIG. 2A.

Figure 2C:
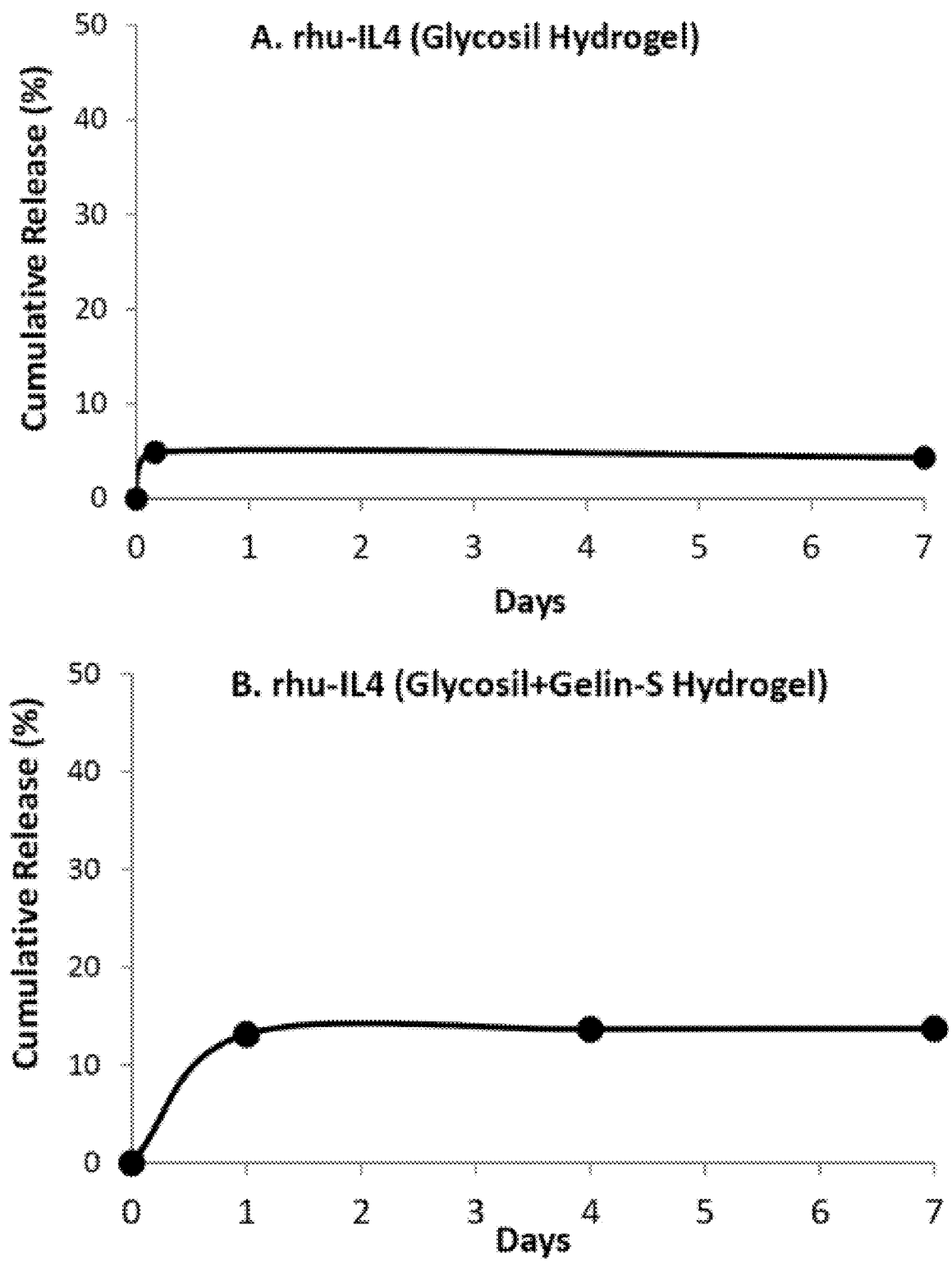

The effect of GLYCOSIL® and GELIN-S® on protein recovery was not an isolated effect observed with GM-CSF. As demonstrated in FIG. 2C, the incorporation of IL-4 protein into the hydrogel also resulted in a marked loss of recoverable protein and the presence of GELIN-S® helped to protect against protein loss. The extremely low recovery of IL4 (~5% from the GLYCOSIL® only hydrogel and ~13% from GLYCOSIL®+GELIN-S® hydrogel) suggests that different proteins have different sensitivities to destruction/denaturation/functional inactivation during the gelation process. It is noteworthy that the IL-4 protein has more disulfide bonds than does GM-CSF, which may account for its greater susceptibility to protein destruction.

Figure 2D:
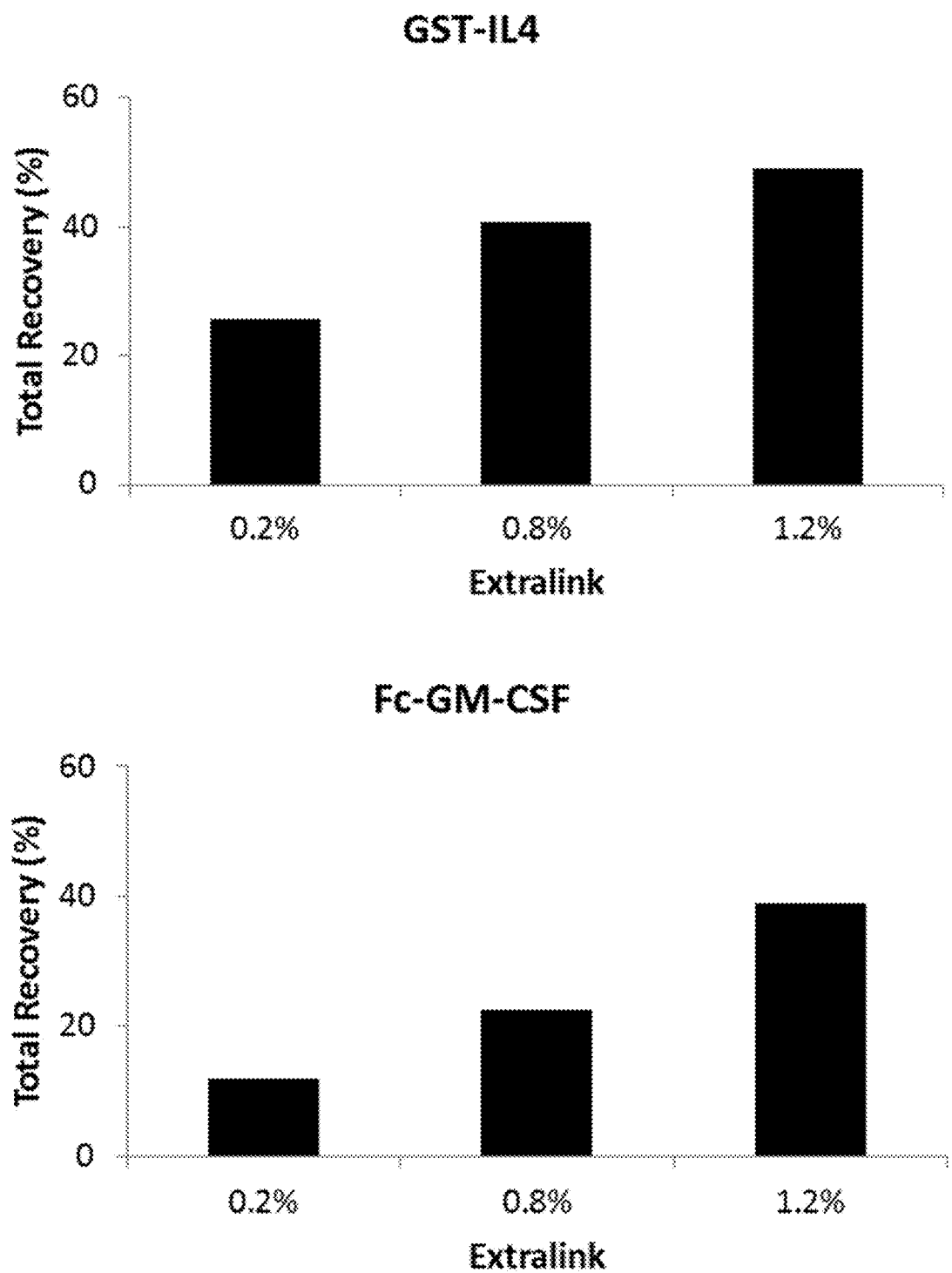

In addition to the protective effect of GELIN-S®, a similar protective effect was observed when the concentration of EXTRALINK® was increased during the formulation of the hydrogel as demonstrated in FIG. 2D. Again, this effect was concentration dependent and occurred irrespective of the specific protein incorporated into the hydrogel.

Without wishing to be bound by theory, these investigations suggest that only a fraction of the protein initially added into the commercially available HA-based hydrogel can be recovered and that this protein loss is primarily due to a chemical reaction with the thiolated hyaluronic acid component which results in protein being degraded/denatured/functionally inactivated. However, this adverse effect on the protein payload can be ameliorated by optimizing the composition and stoichiometry of the final hydrogel constituents. Additives, such as functionalized gelatin (GELIN-S®), can be protective and significantly enhance the release of functional protein. In addition, the stoichiometry between the functionalized HA and the cross-linking reagent (PEGDA) can be adjusted in a manner that further enhances the recovery of viable protein. In an optimal production of a hydrogel that will be used for the delivery of protein-based reagents, the individual constituents of the hydrogel and any additives should be optimized in a manner that promotes the recovery of a high fraction of the loaded protein payload.

Example 3. Cross-Linking Density can Control Protein Retention

The pore size of a HA-based hydrogel is dependent upon the degree of cross-linking that occurs between the HA (GLYCOSIL®) and PEGDA (EXTRALINK®) constituents. In the texted commercial HA-based hydrogel, the concentration of thiolated sites present on the HA constituent is always in molar excess compared to the frequency of reactive sites within the added PEGDA. Without wishing to be bound by theory, this may explain why the toxic effects of GLYCOSIL® on added protein are quenched in the presence of both GELIN-S® and PEGDA, both of which react with and neutralize the free thiol groups present on the HA component. Similarly, this stoichiometry may explain why the addition of higher concentrations of PEGDA promotes greater cross-linking with the HA constituent and smaller effective pore size. At relatively low concentrations of EXTRALINK® (0.2 to 0.4 w/v) pore size has been reported to be several microns while conventional proteins in the size range of 10-30 kd exhibit effective diameters in the nanometer range. Further, our studies failed to find any significant retention of standard proteins when loaded into a conventional hydrogel formulation as noted above. However, without wishing to be bound by theory, it is believed that by increasing the concentration of PEGDA and simultaneously increasing the effective size of proteins by fusing them to carrier proteins (protein tagging), a point may be reached where size-based retention does occur within the hydrogel matrix and results in a slower and more controlled protein release. A proof of concept experiment is shown in FIG. 3A, where a clear decrease in the rate of protein release was observed from hydrogels formulated with EXTRA-LINK® at a concentration of 1.2% (w/v) vs. 0.8% when loaded with an IL-4 protein fusion construct that has a molecular weight that is more than double that of IL-4.

The concentration of EXTRALINK® that can be employed is limited by the concurrent effect that it has on the rate of cross-linking. Gelation cannot occur too quickly if the hydrogel is to be mixed, loaded, and injected at a desired tissue site before it starts to transition to a solid gelled state. On the other hand, protein fusion constructs can be generated in a variety of sizes, extending the potential to match protein size with desired release characteristics.

To assess the importance of matching/adjusting protein size to achieve desired retention and release characteristics different molecular weight constructs were artificially constructed based on the use of different sized proteins and protein-specific antibody binding. As noted in FIGS. 3B and 3C, the release kinetics were very similar when a GM-CSF-antibody Fc sequence fusion construct of 41 kD size was compared to an IL-4-Fc sequence construct of 43 kD. However, when their release from the hydrogel was compared to that of an ICAM-1-Fc fusion construct of approximately 78 kD, there was a significant size-related slowing in protein release. (FIG. 3B). These data suggested that larger molecules are released from an appropriately cross-linked hydrogel in a more sustained manner. Then, anti-Fc sequence antibody was added to the Fc-IL4 fusion construct to produce an antibody-protein conglomerate. The ratio of Fc-IL-4 to anti-Fc antibody was varied from 1:1 to 1:5 to produce more efficient binding and determine the impact of the conglomerate size on protein release. When these different "formulations" of IL-4 were encapsulated into the hydrogel there was clear impact of the antibody-Fc-IL-4 conglomerate on the release kinetics such that a slow and continued release was observed over a period of two weeks rather than complete release within the first 2 days (FIG. 3C).

Without wishing to be bound by theory, it is believed that intact antibodies, with a molecular weight of approximately 150 kD, might provide an optimal-sized reagent for sustained release from a modified hydrogel matrix. FITC-conjugated anti-Cytokeratin antibodies were formulated into hydrogel (GLYCOSIL® [0.4% w/v], GELIN-S® [0.4% w/v], EXTRALINK® [1.2% w/v]) and incubated at 37° C. for 3 days flowed by lysing the hydrogel with HAse (FIG. 3D). These anti-cytokeratin antibodies were released from the hydrogel matrix in a controlled manner over the course of 3 days. In addition, when the anti-Cytokeratin antibodies pre-incubated with secondary antibodies to increase the molecular size, release from hydrogel was further slowed. These data demonstrated that the size of the protein affects its release and suggest that sustained antibody release over a period from days to weeks can be achieved by increasing the size characteristics of the antibody or employing antibody constructs or multimers.

Without wishing to be bound by theory, it is believed that one method to produce optimal HA-based hydrogels that will be used for the sustained local delivery of protein-based reagents, one may increase the cross-linking density by optimizing the concentration of cross-linking reagent to reduce the pore size of the gel matrix (in this case PEGDA used in the range of 1.2% w/v) and appropriately match the gel porosity with the functional size of the protein that will be incorporated and delivered as the payload. In this respect, antibodies may be considered as an example of an optimally sized protein reagent with biologic activity that can be loaded into such a hydrogel and delivered by passive diffusion in a slow-release manner. Similarly, other proteins of interest with biologic activity can be appropriately modified for delivery by a hydrogel by creating conjugates (tagged proteins) with human immunoglobulin (Ig) proteins or their sub-units as a mechanism for controlling their retention and release from the hydrogel matrix. Such proteins are known to retain their biologic activity.

Example 4. Protein Conjugates Containing a GST Tag can Increase Protein Retention In order to avoid rapid release and to achieve sustained release of protein reagents that have a smaller molecular weight an affinity-ligand approach was evaluated: Gluta-thione-S-transferase (GST) is a natural protein present in almost all organisms that has a high affinity for and is involved in the reduction of reactive thiol groups and glutathione. Given that GLYCOSIL® is a heavily thiolated form of hyaluronic acid, without wishing to be bound by theory, it was believed that GST-tagged proteins would specifically interact with the HA-hydrogel matrix resulting in an affinity-based retention without the need to add other types of ligand components to the hydrogel matrix. In addition, as a protein of approximately 26 kD, other proteins of interest once conjugated to GST might also have a size advantage with respect to their retention. The GST-tag is frequently used to expedite protein purification and a number of GST-tagged protein reagents are already available for investigation which adds to the relevance of this specific approach. Different hydrogel formulations were prepared, focusing on increasing the concentration of PEGDA to decrease pore size and protect added proteins from denaturation/destruction/functional inactivation, and their retention and release of GST-tagged proteins were examined. GST-GM-CSF and GST-IL-4 were examined for this purpose. As in other studies, exogenous hyaluronidase was added at the end of the assay to digest the gels and release any cytokine that still remained within the hydrogel matrix at that point in time. As shown in FIGS. 4A and 4B, both the amount of these GST constructs and their rate of release were less than that observed with native GM-CSF and IL-4 and increased with the concentration of EXTRALINK®. Furthermore, substantial amounts of these protein constructs were retained at the end of a week and only released following digestion with hyaluronidase, suggesting avid retention within the hydrogel matrix in a manner not accounted for based on their molecular weight alone. The relative release between 24 hr and day 7 decreased as the concentration of EXTRALINK® increased. Seven days after hydrogel formation, ~12% (EXTRALINK® 0.2%), ~25% (EXTRALINK® 0.4%) and 39% (EXTRALINK® 1.2%) of GST-GM-CSF remained in hydrogel.

As noted, the most striking retention occurred when the EXTRALINK® concentration was increased up to 1.2% (w/v) and when the effect on IL-4 release was studied, as much as 73% of the recovered protein remained in hydrogel 7 days after gelation. Without wishing to be bound by theory, the difference between GST-GM-CSF and GST-IL4 may also be related to a protective effect of the higher EXTRALINK® concentration and the protein tag on the recovery of viable protein. As previously noted, unmodified IL-4 is very susceptible to degradation and/or denaturation during the gelation process and can be protected by a number of factors.

Without wishing to be bound by theory, it is believed that one method to produce optimal HA-based hydrogels that will be used as an affinity-based approach for the sustained local delivery of protein-based reagents, one may increase the concentration of the cross-linking reagent (in this case PEGDA used in the range of 1.2% w/v) and/or, as demonstrated by these results, to employ GST-tagged proteins that will specifically bind and be retained by the hydrogel components. This approach does not require any further modification of the hydrogel itself or the addition of any other affinity-based ligands to the gel matrix. This approach also takes advantage of the common practice of using GST-tagging to produce and purify proteins with biologic activity of interest.

Example 5. Hyaluronidase Comprised within the HA-Based Hydrogel Matrix Promotes Auto-Degradation of the Hydrogel and Controls the Rate of Protein Release Having described above two methods focused on retaining proteins within the hydrogel matrix to affect their slow release, one based on size and the other on affinity, it was determined by the inventors herein that an additional modification is useful in order to fine-tune the rate of protein delivery. Rather than focusing on retention, the approach was focused on controlling release. The approach was shown herein to allow the retention and release characteristics of the hydrogel to be independently adjusted in order to fine-tune the overall delivery rate and the time interval over which a protein payload is delivered. Furthermore, without wishing to be bound by theory, in terms of clinical practice, depositing a mass of hyaluronic acid to a tissue site might be problematic if that mass persisted for weeks to months; however, a self-resorbing hydrogel might address this issue.

In order to address these specific issues, the impact of incorporating hyaluronidase directly into the hydrogel was examined regarding the ability to produce a controlled auto-degradartion of the hyaluronic acid matrix. As an initial proof of concept, different amounts of hyaluronidase (0, 2 or 6 units) were incorporated into hydrogels and their degradation was evaluated by assessing the remaining volume of each gel over time. Release media was removed at each time point, (24 hr, 3 days and 5 days). A drop of trypan blue dye was added to visualize the remaining gel. In the absence of hyaluronidase, there was no change in gel volume over time. However, the addition of hyaluronidase produced a time and dose dependent decrease in gel volume.

This data supports that a HA-based hydrogel can be designed to deliver protein reagents and that the incorporation of an optimal concentration of hyaluronidase can be used to promote self-resorption over a defined time period. To test this hypothesis, GST-GM-CSF was incorporated into a hydrogel along with different amounts of hyaluronidase (0.5, 1, or 2.5 units). Hydrogels formulated in this manner were incubated in release media at 37oC for 7 days followed by adding additional hyaluronidase into the media during the last 24 hrs to completely lyse the hydrogel and release any protein still retained at that time (FIG. 5B). Very specific effects on protein release were observed that were directly dependent upon the amount of hyaluronidase incorporated into the hydrogel. Higher amounts of hyaluronidase led to greater release during the first 4 hrs (so-called initial bolus release) and to a faster overall rate of protein release during the 7 day culture period. Furthermore, the more hyaluronidase added, the lower the level of protein still retained by the hydrogel matrix at the end of the 7 day culture period. This data confirmed that the release rate of proteins retained within the hydrogel matrix, in this case the protein was retained due to the incorporation of a GST-based affinity tag, and duration of their release can be specifically adjusted by controlling the amount of hyaluronidase to be formulated into the HA-based hydrogel.

As hyaluronidase is a degrading enzyme, we wanted to assure that adding it to the hydrogel did not adversely impact on the recovery of viable protein. Surprisingly, adding higher concentrations of hyaluronidase actually promoted more effective recovery of intact protein. This effect was directly assessed by adding different amounts of hyaluronidase (0.5, 1 and 2.5 units) to the hydrogel and measuring the release of GST-GM-CSF in vitro into release media. As shown in FIG. 5C, we observed that the higher the amount of hyaluronidase added, the higher the total recovery of protein. Compared to the control hydrogel without hyaluronidase, the total recovery of GST-GM-CSF from hydrogels was increased to 180.0% (0.5 unit), 219.0% (1 unit) and 266.5% (2.5 units), respectively. These results suggest that hyaluronidase has a protective effect on the degradation/denaturation/functional inactivation of added protein that otherwise occurs during the gelation process. While the demonstrated example involved GST-GM-CSF, the same effects were observed with GST-IL-4, suggesting that the effect is general and not specific to the protein added.

Example 6. In Vitro and In Vivo Correlation of Protein Retention and Rate of Protein Release While the above proof of principals were confirmed under in vitro conditions, an important application of this technology will include the injection of hydrogels in vivo as an approach for the sustained local delivery of protein-based biologic reagents. To examine whether the described strategies are likely to apply to the function of hydrogels in vivo, hydrogels containing GM-CSF or GST-GM-CSF, either alone or in the presence of added hyaluronidase (2.5 units), were simultaneously prepared and the release characteristics of the hydrogels were examined when placed into a test-tube in vitro and when administered as a subcutaneous injection in vivo to mice.

To measure the retention/release of GM-CSF and GST-GM-CSF in vitro, the release media was completely removed at 4 hours or at 3 days from replicate tubes and excess hyaluronidase added for 24 hrs to completely lyse the remaining hydrogel. Retained protein content was then measured by ELISA assay.

To measure the retention/release of GM-CSF and GST-GM-CSF in vivo, the hydrogel was surgically-resected from the subcutaneous space (at the site of injection) from replicate animals at either 4 hours or 3 days after injection. The amount of protein retained within the recovered gel was determined by lysing the gel for 24 hrs with an excess of hyaluronidase and measuring by ELISA (FIGS. 6A and 6B).

The cytokine level retained within the hydrogel 4 hours after gelation was 20.4% (GM-CSF), 51.8% (GST-GM-CSF) and 39.5% (GST-GM-CSF/HAse) when assessed using the hydrogels that were cultured in vitro, and 2.1% (GM-CSF), 34.2% (GST-GM-CSF) and 15.1% (GST-GM-CSF/HAse) when assessed using the hydrogels that were recovered from mice following in vivo injection. The cytokine level retained by hydrogel 3 days after gelation was <0.1% (GM-CSF), ~32.2% (GST-GM-CSF) and 4.2% (GST-GM-CSF/HAse) when assessed using the hydrogels that were cultured in vitro, and <0.1% (GM-CSF), ~3.8% (GST-GM-CSF) and 2.0% (GST-GM-CSF/HAse) when assessed using the hydrogels that were recovered from mice following in vivo injection. This proof-of-principal test confirmed that the GST tagged GM-CSF remains in the hydrogels longer compared to the un-modified GM-CSF and that this occurs in the test tube in vitro and when injected into animals and tested in vivo. Similarly, incorporating hyaluronidase into the hydrogel formulation accelerates the release rate that occurs in the test tube in vitro and when injected into animals and tested in vivo. As such, the findings confirm that using the combination of GST-tagged proteins and hyaluronidase can be used to control the retention and release characteristics of a HA-based hydrogel, that such a hydrogel can be delivered as in vivo reservoir for the controlled delivery of protein reagents, and that in vitro modeling can be used to approximate the local tissue delivery characteristics of different gel formulations. By extension, it is reasonable to anticipate that the same conclusions can be applied to the formulation and delivery of protein reagents when the hydrogels are formulated to match gel porosity and protein size as the mechanism for generating a slow release product.

Example 7. Molecular Weight is a Key Determinant of Release Kinetics

To assess the role of protein weight/size as a determinant of subsequent release kinetics from a hyaluronic acid hydrogel, a single hydrogel formulation, GLYCOSIL® hydrogel (GLYCOSIL® [0.8% w/v], EXTRALINK® [1.2% w/v]), was loaded with proteins, protein conjugates, or protein-antibody complexes of various molecular weights as already detailed in Example 3 (FIG. 3B-D). The results suggested an inverse relationship between molecular weight (size) and the rate of release. Furthermore, the data suggested that the molecular weight of a conventional antibody, at approximately 150 kDa, might be optimal for controlled delivery over a period of days to weeks.

To more directly assess the role of molecular weight on release kinetics, in the absence of differences in amino acid composition and 3-dimensional structure, different FITC-labeled dextran constructs varying between 20 to 500 kDa molecular weight as detailed in FIG. 8 (A) were evaluate. As these constructs are all formed from the same components, the major difference between them relates to molecular weight. Again, as when comparing different proteins, there was a direct and inverse relationship between molecular weight and release rate. With the smallest construct (20 kDa), 80% of the loaded FITC-labeled dextran was released into the media by 8 hrs. However, with the medium sized construct (150 kDa) only 50% was released by 8 hrs and release of 80% did not occur until 72 hrs. When the construct was increased in size to 500 kDa, its release from the hydrogel into the media was further slowed. After 8 hrs, only about 30% was released, with only 60% recovery at 72 hrs and 75% recovery after 5 days.

The same relationship between molecular weight and release rate was observed when these different molecular weight constructs of FITC-labeled dextran were incorporated into a hydrogel and injected into the subcutaneous tissue of C57B1/6 mice. Gelation occurred in vivo and a local subcutaneous deposit of hydrogel was formed. These hydrogels were recovered 4 hrs later by surgical excision (FIG. 8 (B)) and the gels placed into tubes with release media to recover residual FITC-labeled dextran that had not yet been released in vivo from the hydrogel. A clear relationship between molecular weight and hydrogel release characteristics was observed and this data directly confirms that molecular weight is a key determinant in the release rate for a hydrogel-encapsulated molecule. A molecular weight of 150 kDa is sufficient to produce a sustained release over several days and the in vitro release assay appears to predict the same relationship that occurs when the hydrogels are injected into the subcutaneous tissue of animals.

Example 8. Controlled Release of Functional Immune Checkpoint Inhibitor Antibodies by a GLYCOSIL® Hydrogel Having confirmed that an antibody construct with a molecular weight of approximately 150 kDa is an appropriate size for producing a controlled release over several days when paired with a specific GLYCOSIL® Hydrogel (GLYCOSIL® [0.8% w/v], EXTRALINK® [1.2% w/v]), the question remained as to the performance characteristics when combined with an antibody of specific clinical interest.

The systemic infusion of antibodies targeting immune checkpoint inhibitors has been shown to produce clinically-significant anti-tumor immunity and prolong the survival of patients with a variety of advanced cancers. However, systemic infusion is associated with the induction of auto-immunity that can produce serious adverse events. Not to be bound by theory, it is hypothesize that the sustained local administration of these therapeutic antibodies using an injectable hydrogel and administered at the site of the tumor and/or draining lymph nodes might produce effective anti-tumor responses while limiting systemic autoimmunity.

To test the hypothesis, the loading, release, and recovery characteristics of the hydrogels disclosed herein were assessed by loading with anti-mouse antibodies directed against the murine CTLA-4 and murine PD-1 checkpoint inhibitor molecules (FIGS. 9 (A) and (B), respectively). For the anti-CTLA-4 antibody, detection and quantitation of the recovered antibody was based on its capacity to bind plate-bound murine anti-CTLA-4. This target-affinity assay therefore provided a readout for both the function and quantity of antibody recovered. The anti-PD-1 antibody was labeled with a FITC marker, which allowed detection and quantitation using a fluorescent plate reader but no measurement of target binding affinity. Both antibodies demonstrated controlled and sustained release from the hydrogel for a period in excess of 3 days. The ultimate recovery of loaded antibody was approximately 100% regardless of whether this was assessed by target binding activity (for anti-CTLA-4) or fluorescent label (for anti-PD-1).

The methods and experimental findings support the conclusion that the characteristics of HA-based hydrogels and their constituents, can be manipulated to control the retention, release, and functional integrity of added protein payloads, and optimal approaches for formulating hydrogels and matched protein reagents as injectable reservoirs for the local and controlled delivery of biologically-active protein payloads. Herein is describe several approaches for matching hydrogel formulations and protein characteristics to achieve retention and sustained release of added protein-based payloads. One is based on hydrogel matrix pore size and matched protein size. For this formulation, antibodies and antibody-based protein fusion constructs are specifically identified as ideal protein reagents for the HA-based hydrogel tested herein. The other is based on using GST-tagged proteins to generate an affinity-based interaction with and retention by the hydrogel matrix. Further, herein is described methods for using additives to protect added proteins from degradation, denaturation, and/or functional inactivation and for adjusting the stoichiometry of the cross-linking constituent to similarly protect added protein from degradation, denaturation, and/or functional inactivation. Finally, herein is described the utility of adding hyaluronidase into the hydrogel formulation as a mechanism for producing a controlled auto-degradation of the hydrogel which can be used to a) resorb hydrogels at a controlled rate after injection; b) control the delivery rate of added protein payloads and c) help protect an protein payload from degradation, denaturation, and/or functional inactivation that otherwise occurs during the gelation process.

Example 9. Controlled Release of Functional Immune Checkpoint Inhibitor Antibodies by a GLYCOSIL® Hydrogel Having confirmed that a GLYCOSIL® [0.8% w/v], EXTRALINK® [1.2% w/v], hydrogel can be used to release antibodies of clinical interest while retaining functional integrity of the antibodies in vitro, in vivo testing was performed to determine if a functionalized HA hydrogel disclosed herein can be effectively used in therapies using active proteins. Specifically, based on the results disclosed above and not to be bound by theory, it is believed that local injection of a hydrogel disclosed herein encapsulating anti-CTLA-4 mAb will:

1) Target local lymphatics and saturate tumor-draining lymph nodes with anti-CTLA-4 mAb over a period of several days;
2) Unleash regional anti-tumor responses by activating and releasing tumor-specific T cells that are concentrated in tumor-draining lymph nodes but otherwise actively suppressed by the tumor, and lead to dissemination of tumor-specific effector cells and changes in tumor infiltrating lymphocytes (TIL);
3) Result in a significant reduction in the systemic exposure to anti-CTLA-4 mAb, as compared to the dose of anti-CTLA-4 mAb that would be required for standard systemic therapy, and thereby reduce the induction of systemic autoimmune toxicity; and
4) Enhance the clinical utility and safety of anti-CTLA-4 therapy when used alone and in particular when anti-CTLA-4 is combined with systemic anti-PD-1 mAb.

To test this hypothesis, an injectable hyaluronic acid-based hydrogel (HA [0.8% w/v], PEGDA [1.2% w/v]) was formulated to deliver, in a time-controlled manner, low-doses of anti-CTLA-4 mAb to tumor-draining lymph nodes in an animal model of colon carcinoma.

Hydrogel-encapsulated anti-CTLA-4 mAb was injected into the peri-tumoral subcutaneous tissue in C57BL/6 mice bearing subcutaneous MC-38 (colon carcinoma cell line) tumors (FIGS. 10A, 10B, and 10C). The MC-38 mouse model is often used by researchers for studying antitumor immunity by immune checkpoints inhibitors. Control mice received no therapy while mice in the experimental groups were injected either 1) in a peri-tumoral location with anti-CTLA4 mAb (50 µg) incorporated into a either a 150 µl hydrogel (on treatment day 0 and 5, total dose of 100 µg) or in PBS (the control condition that delivers antibody but without the controlled release afforded by the hydrogel, also delivered on treatment day 0 and 5, total dose of 100 µg) (FIGS. 10A and 10C), or
2) in a standard systemic treatment approach which involved 200 µg of the anti-CTLA-4 mAb in PBS as an intraperitoneal injection on treatment days 0, 3, and 9 (total dose 600 µg (FIGS. 10B and 10C).

As shown in the FIGS. 10A-10C, regional administration of anti-CTLA-4 mAb encapsulated in the hydrogel significantly suppressed tumor growth over 3-4 weeks as compared to a) the untreated tumor-bearing control group (p<0.05) and b) the local therapy control group treated with anti-CTLA-4 mAb delivered in PBS (p<0.05) (FIG. 10A). With respect to tumor growth rate, treatment with a total of 100 µg of anti-CTLA-4 delivered by hydrogel appeared equal to or slightly better than standard systemic therapy that used 600 µg of anti-CTLA-4 (FIG. 10B). The survival curves (FIG. 10C) also demonstrate the superior protection from tumor afforded by the regional administration of anti-CTLA-4 mAb when encapsulated in the hydrogel.

Taken together these studies demonstrate that a specifically-formulated HA-hydrogel (formulation (HA [0.8% w/v], PEGDA [1.2% w/v]) loaded with a therapeutic anti-CTLA-4 mAb results in a controlled and sustained release of anti-CTLA-4 mAb over a period of 3-5 days. The administered dose, approximately 16% of the established systemic dose for this model, also produced a robust antitumor response that appeared equal to or slightly better than the response produced by the larger systemic dose. It is expected that utilizing hydrogel-encapsulated antibodies against immune checkpoint inhibitors, such as anti-CTLA-4, anti-PD-1, anti-PDL-1, or a combination thereof as a regional injection administered to the peri-tumor tissue will enhance the clinical utility and safety of this established cancer therapy. Such hydrogel-encapsulated antibodies can be used alone or in combination with systemic administration of antibodies, such as anti-CTLA-4, anti-PD-1, and/or anti-PD-L1 antibodies, or administration of other therapies. As demonstrated above, use of the hydrogels disclosed herein can be applicable to other antibodies that target immune checkpoint inhibitors, such as anti-PD-1 antibodies (see FIG. 9 (B)). A number of mAbs targeting other checkpoint inhibitors are in various stages of development and human testing.

Example 10. Additional Assays

The following additional assays are currently planned and can be used as additional proof of concept for use of hydrogel-encapsulated antibodies as effective therapies. These experiments can be performed using similar methods to those disclosed above in Example 9.

a) A repeat mouse tumor experiment that includes a dose titration of hydrogel encapsulated anti-CTLA-4 at doses of 25, 50 and 100 μg to identify the lowest dose that is equally effective and/or whether increasing the dose will produce a statistically-superior response as compared to standard systemic therapy.

b) A mouse tumor experiment that combines an optimal dose of hydrogel-encapsulated anti-CTLA-4 with systemic therapy using anti-PD-1 mAb to address whether this combination demonstrates the same dose advantage as does therapy with anti-CTLA-4 alone.

c) Test to examine the biology of regional anti-CTLA-4 therapy on T cell activation and tumor infiltration and to directly address the impact on the risk/benefit ratio by comparing the toxicity of standard systemic therapy to that produced by low-dose regional therapy in a model of anti-CTLA-4 mediated thyroiditis and the generation of pathologic antithyroid antibody titers.

To examine the impact on autoimmune toxicity that is often associated with systemic administration of anti-CTLA-4 mAb, NOD.H-2h4 mice will be examined for the effects of treatment on the development of autoimmune thyroiditis. NOD.H-2h4 mice develop a low frequency of thyroiditis when drinking water is supplemented with iodine and this effect is exacerbated in a dose-dependent manner by systemic administration of anti-CTLA-4 mAb. NOD.H-2h4 mice will be administered iodine supplemented water and treated with either 1) saline as a negative control; 2) systemic anti-CTLA-4 mAb alone or in combination with anti-PD-1 mAb as a positive control; or regional hydrogel-encapsulated anti-CTLA-4 mAb alone or in combination with systemic anti-PD-1 mAb. Autoimmune thyroiditis will be assessed by evaluating the serum level of thyroglobulin autoantibody (ELISA) and by histopathological appearance of the thyroid gland. Similarly, MC-38 tumor bearing C57BL6 mice will receive the same treatments to evaluate the effects of single vs combination therapy on tumor growth/animal survival.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Biolegend Technical data sheet LEGEND MAX™ Human GM-CSF ELISA Kit with Pre-coated Plates (http://www.biolegend.com/legend-max-human-gm-csf-elisa-kit-5828.html)

Borghaei H, Paz-Ares L, Horn L, et al. Nivolumab versus docetaxel in advanced nonsquamous non-small-cell lung cancer. N Engl J Med. 2015; 373(17):1627-39.

Cai S, et al. Injectable glycosaminoglycan hydrogels for controlled release of human basic fibroblast growth factor. Biomaterials. 2005; 26(30):6054-67.

Gettinger S N, Horn L, Gandhi L, et al. Overall survival and long-term safety of nivolumab (anti-programmed death-1 antibody, BMS-936558, ONO-4538) in patients with previously treated advanced non-small-cell lung cancer. J Clin Oncol. 2015; 33:2004-12.

Hellmann M D, Rizvi N A, Goldman J W, Gettinger S N, Borghaei H, Brahmer J R, Ready N E, Gerber D E, Chow L Q, Juergens R A, Shepherd F A, Laurie S A, Geese W J, Agrawal S, Young T C, Li X, Antonia S J. Nivolumab plus ipilimumab as first-line treatment for advanced non-small-cell lung cancer (CheckMate 012): results of an open-label, phase 1, multicohort study. Lancet Oncol. 2017; 18(1):31-41.

Hodi F S, Chesney J, Pavlick A C, Robert C, Grossmann K F, McDermott D F, Linette G P, Meyer N, Giguere J K, Agarwala S S, Shaheen M, Ernstoff M S, Minor D R, Salama A K, Taylor M H, Ott P A, Horak C, Gagnier P, Jiang J, Wolchok J D, Postow M A. Combined nivolumab and ipilimumab versus ipilimumab alone in patients with advanced melanoma: 2-year overall survival outcomes in a multicentre, randomised, controlled, phase 2 trial. Lancet Oncol. 2016; 17(11):1558-1568.

Hodi F S, O'Day S J, McDermott D F, et al. Improved survival with ipilimumab in patients with metastatic melanoma. N Engl J Med. 2010; 363:711-723.

Larkin J, Chiarion-Sileni V, Gonzalez R, et al. Combined nivolumab and ipilimumab or monotherapy in untreated melanoma. N Engl J Med. 2015; 373(1):23-34.

Ledford H. Cocktails for cancer with a measure of immunotherapy. Nature. 2016; 532(7598):162-64.

Linch S N, Kasiewicz M J, McNamara M J, Hilgart-Martiszus I F, Farhad M, Redmond W L. Combination OX40 agonism/CTLA-4 blockade with HER2 vaccination reverses T-cell anergy and promotes survival in tumor-bearing mice. Proc Natl Acad Sci USA. 2016; 113(3):E319-27.

McDermott D F, Drake C G, Sznol M, et al. Survival, durable response, and long-term safety in patients with previously treated advanced renal cell carcinoma receiving nivolumab. J Clin Oncol. 2015; 33:2013-20.

Page D B, Postow M A, Callahan M K, Allison J P, Wolchok J D. Immune modulation in cancer with antibodies. Annu Rev Med. 2014; 65:185-202.

Peattie R A, et al. Effect of gelatin on heparin regulation of cytokine release from hyaluronan-based hydrogels. Drug Deliv. 2008; 15(6):389-97.

Pike D B, et al. Heparin-regulated release of growth factors in vitro and angiogenic response in vivo to implanted hyaluronan hydrogels containing VEGF and bFGF. Biomaterials. 2006; 27(30):5242-51.

Postow M A, Chesney J, Pavlick A C, Robert C, Grossmann K, McDermott D, Linette G P, Meyer N, Giguere J K, Agarwala S S, Shaheen M, Ernstoff M S, Minor D, Salama A K, Taylor M, Ott P A, Rollin L M, Horak C, Gagnier P, Wolchok J D, Hodi F S. Nivolumab and ipilimumab versus ipilimumab in untreated melanoma. *N Engl J Med.* 2015; 372(21):2006-17.

Rakhmilevich A L, Felder M, Lever L, Slowinski J, Rasmussen K, Hoefges A, Van De Voort T J, Loibner H, Korman A J, Gillies S D, Sondel P M. Effective Combination of Innate and Adaptive Immunotherapeutic Approaches in a Mouse Melanoma Model. *J Immunol.* 2017; 198(4):1575-1584.

Ribas A, Puzanov I, Dummer R, et al. Pembrolizumab versus investigator-choice chemotherapy for ipilimumab-refractory melanoma (KEYNOTE-002): a randomised, controlled, phase 2 trial. *Lancet Oncol.* 2015; 16:908-918.

Schadendorf D, Hodi F S, Robert C, et al. Pooled analysis of long-term survival data from phase II and phase III trials of ipilimumab in unresectable or metastatic melanoma. *J Clin Oncol.* 2015; 33(17):1889-94.

Selby M J, Engelhardt J J, Johnston R J, Lu L S, Han M, Thudium K, Yao D, Quigley M, Valle J, Wang C, Chen B, Cardarelli P M, Blanset D, Korman A J. Correction: Preclinical Development of Ipilimumab and Nivolumab Combination Immunotherapy: Mouse Tumor Models, In Vitro Functional Studies, and Cynomolgus Macaque Toxicology. *PLoS One.* 2016; 11(11):e0167251.

Tivol E A, Borriello F, Schweitzer A N, Lynch W P, Bluestone J A, Sharpe A H. Loss of CTLA-4 leads to massive lymphoproliferation and fatal multiorgan tissue destruction, revealing a critical negative regulatory role of CTLA-4. *Immunity.* 1995; 3(5):541-47.

Waterhouse P, Penninger J M, Timms E, Wakeham A, Shahinian A, Lee K P, Thompson C B, Griesser H, Mak T W. Lymphoproliferative disorders with early lethality in mice deficient in Ctla-4. *Science.* 1995; 270(5238):985-88.

Weber J S, D'Angelo S P, Minor D, et al. Nivolumab versus chemotherapy in patients with advanced melanoma who progressed after anti-CTLA-4 treatment (CheckMate 037): a randomised, controlled, open-label, phase 3 trial. *Lancet Oncol.* 2015; 16:375-384.

Xu et al. Hyaluronic Acid-Based Hydrogels: from a Natural Polysaccharide to Complex Networks. *Soft Matter.* 2012; 8(12): 3280-3294.

The invention claimed is:

1. A method of treating a subject suffering from tumor(s) comprising administering to a subject a composition as a liquid capable of in situ formation of a hyaluronic acid-based hydrogel that comprises:
   a) a porous cross-linked polymeric matrix comprising 0.2% w/v to 1% w/v thiol-modified hyaluronic acid and 0.6% w/v to 1.6% w/v polyethylene glycol diacrylate, wherein the thiol-modified hyaluronic acid is cross-linked with the polyethylene glycol diacrylate; and
   b) an anti CTLA-4 antibody entrapped in the pores of the polymeric matrix.

2. The method of claim 1, wherein the anti CTLA-4 antibody is capable of being released in a controlled manner from the formed hydrogel and the composition is administered to a target tissue or organ to perfuse immune cells within the target tissue or organ with the anti CTLA-4 antibody.

3. The method of claim 2, wherein the method further comprises administering to the subject an additional antibody different than the CTLA-4 antibody, wherein the additional antibody targets an immune checkpoint pathway.

4. The method of claim 3, wherein the additional antibody is one or more of an anti PD-1 antibody, anti TGIT antibody, anti 4-Ibb antibody, anti CD27 antibody, anti GTIR antibody, anti OX40 antibody, anti TIM3 antibody, and/or anti PD-L1 antibody.

5. The method of claim 1, wherein the anti CTLA-4 antibody has a molecular weight of 40 kD to 170 kD.

6. The method of claim 1, wherein the composition further comprises a molecule with hyaluronidase activity.

7. The method of claim 3, wherein the additional antibody is encapsulated in the hyaluronic acid-based hydrogel formed and/or in a second hyaluronic acid-based hydrogel formed in situ, the second formed hyaluronic acid-based hydrogel comprising a porous cross-linked polymeric matrix of 0.2% w/v to 1% w/v thiol-modified hyaluronic acid and 0.6% w/v to 1.6% w/v polyethylene glycol diacrylate, wherein the thiol-modified hyaluronic acid is cross-linked with the polyethylene glycol diacrylate.

8. The method of claim 1, wherein the subject is treated for regulating an immune system and/or the role of an immune response in the treatment of a disease.

9. The method of claim 6, wherein the concentration of the molecule with hyaluronidase activity is capable of decreasing a rate of degradation, denaturation, and/or functional inactivation of the anti CTLA-4 antibody comprised in the formed hyaluronic acid-based hydrogel when compared to a same hyaluronic acid-based hydrogel without a molecule with hyaluronidase activity.

10. The method of claim 1, wherein the composition further comprises a gelatin and/or functionalized gelatin.

11. The method of claim 10, wherein the concentration of the gelatin and/or functionalized gelatin is capable of modulating gelation time and/or rate of auto-degradation of the formed hyaluronic acid-based hydrogel when compared to a same hyaluronic acid-based hydrogel without gelatin or functionalized gelatin.

12. The method of claim 10, wherein the concentration of the gelatin and/or functionalized gelatin is capable of slowing degradation, denaturation, and/or functional inactivation of the anti CTLA-4 antibody comprised in the formed hyaluronic acid-based hydrogel when compared to a same hyaluronic acid-based hydrogel without gelatin or functionalized gelatin.

13. The method of claim 10, wherein the composition comprises 0.1% w/v to 0.8% w/v of the functionalized gelatin.

14. The method of claim 1, wherein the method further comprises administering an antibody or a fusion antibody different than the CTLA-4 antibody, a cytokine or a fusion cytokine, a chemokine or a fusion chemokine, a growth factor or a fusion growth factor, or a hormone or fusion hormone.

15. The method of claim 14, wherein the method comprises administering a cytokine, wherein the cytokine is a human Fc conjugated cytokine with immune activating properties.

16. The method of claim 1, wherein the anti CTLA-4 antibody has a molecular weight of 130 kD to 170 kD.

17. The method of claim 4, wherein the method comprises systemically administering an anti PD-1 antibody.

18. The method of claim 1, wherein the composition is administered to the subject at a tumor site, at a site of a lymph node that drains a tumor, and/or in a tissue distribution of a lymph node that drains a tumor.

19. The method of claim 18, wherein administration of the composition is a method for regulating the immune system and/or the role of an immune response in the treatment of a disease.

20. The method of claim 8, wherein the disease treated is cancer and administration of the composition to the subject regulates the immune system and/or the role of an immune response in the subject.

* * * * *